US008815885B2

(12) United States Patent
Walter et al.

(10) Patent No.: US 8,815,885 B2
(45) Date of Patent: Aug. 26, 2014

(54) METHODS AND COMPOSITIONS FOR MODULATING IRE1, SRC, AND ABL ACTIVITY

(75) Inventors: Peter Walter, San Francisco, CA (US); Alexei Korennykh, San Francisco, CA (US); Kevan M. Shokat, San Francisco, CA (US); Chao Zhang, Santa Cruz, CA (US); Janet Finer-Moore, San Bruno, CA (US); Robert Stroud, San Francisco, CA (US); Pascal Egea, San Francisco, CA (US); Andrei Korostelev, Santa Cruz, CA (US); Arvin Dar, San Francisco, CA (US); Sebastian Bernales, Santiago (CL)

(73) Assignee: The Regents of the University of California, Oakland, CA (US)

( * ) Notice: Subject to any disclaimer, the term of this patent is extended or adjusted under 35 U.S.C. 154(b) by 532 days.

(21) Appl. No.: 13/119,162

(22) PCT Filed: Sep. 15, 2009

(86) PCT No.: PCT/US2009/056993
§ 371 (c)(1),
(2), (4) Date: Sep. 12, 2011

(87) PCT Pub. No.: WO2010/031056
PCT Pub. Date: Mar. 18, 2010

(65) Prior Publication Data
US 2011/0319436 A1 Dec. 29, 2011

Related U.S. Application Data

(60) Provisional application No. 61/097,173, filed on Sep. 15, 2008.

(51) Int. Cl.
*C07D 403/12* (2006.01)
*A61K 31/4155* (2006.01)
(52) U.S. Cl.
CPC ........... *C07D 403/12* (2013.01); *A61K 31/4155* (2013.01)
USPC ......................................... 514/275; 544/324
(58) Field of Classification Search
CPC ........................... C07D 403/12; A61K 31/4155
USPC ........................................... 544/324; 514/275
See application file for complete search history.

(56) References Cited

U.S. PATENT DOCUMENTS

| 4,861,760 A | 8/1989 | Mazuel et al. |
| 4,911,920 A | 3/1990 | Jani et al. |
| 5,212,162 A | 5/1993 | Missel et al. |
| 5,403,841 A | 4/1995 | Lang et al. |

FOREIGN PATENT DOCUMENTS

| JP | 2004-518703 A | 6/2004 |
| JP | 2008-526759 A | 7/2008 |
| WO | 96/05309 A2 | 2/1996 |
| WO | 02/62789 A1 | 8/2002 |
| WO | 03/026664 A1 | 4/2003 |
| WO | 03/026665 A1 | 4/2003 |
| WO | 2006/074057 A2 | 7/2006 |
| WO | 2008/005538 A2 | 1/2008 |

OTHER PUBLICATIONS

Statsuk et al., Tuning a Three-Component Reaction for Trapping Kinase Substrate Complexes, J. Am. Chem. Soc. 2008, 130. pp. 17568-17574.*
Australian Office Action issued in International Patent Application No. 2009290617, dated Aug. 26, 2013, 5 pages.
Statsuk, Alexander V. et al., "Tuning a Three-Component Reaction for Trapping Kinase Substrate Complexes", *Journal of the American Chemical Society* 2008, 130(51):17568-17574.
International Search Report and the Written Opinion of the International Searching Authority issued in Patent Application No. PCT/US2009/056993, dated Jun. 10, 2010, 12 pages.
International Preliminary Report on Patentability issued in Patent Application No. PCT/US2009/056993, dated Mar. 24, 2011, 9 pages.
Chinese Office Action issued in International Patent Application No. 200980145225.3, dated Feb. 6, 2013, 16 pages.
EPO Search Report issued in International Patent Application No. 09813799.5, dated May 22, 2012.
Aragón, Anthony D. et al., "Characterization of Differentiated Quiescent and Nonquiescent Cells in Yeast Stationary-Phase Cultures", *Molecular Biology of the Cell* 19:1271-1280, 2008.
Aragón, Anthony D. et al., "Microarray based analysis of temperature and oxidative stress induced messenger RNA in *Schistosoma mansoni*", *Molecular & Biochemical Parasitology* 162:134-141, 2008.
Aragón, Tomas et al., "Messenger RNA targeting to endoplasmic reticulum stress signaling sites", Nature 457(7230):736-740, 2009.
Berge, Stephen M. et al., "Pharmaceutical Salts", Journal of Pharmaceutical Sciences Berge et al., "Pharmaceutical Salts", *Journal of Pharmaceutical Sciences* 66(1):1-19, 1977.
Cox, Jeffery S. et al., "A Novel Mechanism for Regulating Activity of a Transcription Factor That Controls the Unfolded Protein Response", *Cell* 87:391-404, 1996.
Credle, Joel J. et al., "On the mechanism of sensing unfolded protein in the endoplasmic reticulum", *Proceedings of the National Academy of Sciences* 102(52):18773-18784, 2005.
Doody, Gina M. et al., "BLIMP-1 is a target of cellular stress and downstream of the unfolded protein response", *European Journal of Immunology* 36:1572-1582, 2006.
Extended European Search Report dated Jun. 8, 2012 for European Application No. 09813799.5, 14 pages.
Fingl, E., et al. "General Principles", *The Pharmacological Basis of Therapeutics*, Fifth Edition (1975), Ch. 1, 1-46.
Gonzalez, Tania N. et al., "Ire1p: A Kinase and Site-Specific Endoribonuclease", *Methods in Molecular Biology* 160:25-36, 2001.

(Continued)

*Primary Examiner* — Deepak Rao
(74) *Attorney, Agent, or Firm* — Kilpatrick Townsend & Stockton LLP

(57) ABSTRACT

Disclosed herein are, inter alia, compositions for modulating Ire1, Src, or Abl, methods for identifying modulating activity in test compounds, and methods for treating diseases caused by the activity or inactivity of Ire1, Src, or Abl.

17 Claims, 23 Drawing Sheets

(56) References Cited

OTHER PUBLICATIONS

Kimata, Yukio et al., "Two regulatory steps of ER-stress sensor Ire 1 involving its cluster formation and interaction with unfolded proteins", *The Journal of Cell Biology* 179(1):75-86, 2007.
Koong, Albert C. et al., "Targeting XBP-1 as a Novel Anti-Cancer Strategy", *Cancer Biology & Therapy* 5(7):756-759, 2006.
Kudo, Takashi et al., "The Unfolded Protein Response os Involved in the Pathology of Alzheimer's Disease", *New York Academy of Sciences* 977:349-355, 2002.
Lee, Kenneth P.K. et al., "Structure of the Dual Enzyme Ire1 Reveals the Basis for the Catalysis and Regulation in Nonconventional RNA Splicing", *Cell* 132:89-100, 2008.
Lin, Jonathan H. et al., "IRE1 Signaling Affects Cell Fate During the Unfolded Protein Response", *Science* 318:944, 2007.
Ma, Yanjun et al., "The role of the unfolded protein response in tumour development: friend or foe?", *Nature Reviews Cancer* 4:966-977, 2004.
Naidoo, Nirinjini et al., "Sleep deprivation induces the unfolded protein response in mouse cerebral cortex", *Journal of Neurochemistry* 92:1150-1157, 2005.
Nock, S. et al., "[1] Purification and Activity Assays of the Catalytic Domains of the Kinase/ Endoribonuclease Ire1p from *Saccharomyces cerevisiae*", *Methods Enzymol* 342:3-10, 2001.
Papa, Feroz R. et al., "Bypassing a Kinase Activity with an ATP-Competitive Drug", *Science* 302:1533-1537, 2003.
Shamu, Caroline E. et al., "Oligomerization and phosphorylation of the Ire1p kinase during intracellular signaling from the endoplasmic reticulum to the nucleus", *The EMBO Journal* 15(12):3028-3039, 1996.
Sidrauski, C. et al., "The Transmembrane Kinase Ire1p Is a Site-Specific Endonuclease That Initiates mRNA Splicing in the Unfolded Protein Response", *Cell* 90:1031-9, 1997.
Yoshida, Hiderou et al., "XBP1 mRNA Is Induced by ATF6 and Spliced by IRE1 in Response to ER Stress to Produce a Highly Active Transcription Factor", *Cell* 107:881-891, 2001.
Zhang, Xuewu et al., "An Allosteric Mechanism for Activation of the Kinase Domain of Epidermal Growth Factor Receptor", *Cell* 125:1137-1149, 2006.
Zheng, Yi et al., "Hepatitis C Virus Non-structural Protein NS4B Can Modulate an Unfolded Protein Response", *The Journal of Microbiology* 43(6):529-536, 2005.
Office Action issued in Japanese Patent Application No. 2011-527045, dated Feb. 18, 2014, 7 pages.

* cited by examiner

Ire1KR32    Ire1KR24              Ire1KR

[P]EKKKKRKRGSRGGKKGRKSRIANIPNFEQSLKNLVVSEKILGYGSSGTVVFQGSFQGRPVAVKRMLIDF

CDIALMEIKLLTESDDHPNVIRYYCSETTDRFLYIALELCNLNLQDLVESKNVSDENLKLQKEYNPISLLRQI

*αD' helix*

ASGVAHLHSLKIIHRDLKPQNILVSTSSRFTADQQTGAENLRILISDFGLCKKLDSCDSSRTNLNNPSGTS

*activation loop*

GWRAPELLEESNNLQCQVETEHSSSRHTVVSSDSFYDPFTKRRLTRSIDIFSMGCVFYYILSKGKHPFGD

KYSRESNIIRGIFSLDEMKCLHDRSLIAEATDLISQMIDHDPLKRPTAMKVLRHPLFWPKSKKLEFLLKVSDR

*αG' helix α3'-α4 loop*

LEIENRDPPSALLMKFDAGSDFVIPSGDWTVKFDKTFMDNLERYRKYHSSKLMDLLRALRNKYHHFMDLP

EDIAELMGPVPDGFYDYFTKRFPNLLIGVYMIVKENLSDDQILREFLYS

[P] is part of the Prescission Protease cleavage site
Kinase
RNase

FIGURE 7

XBP1 (443 nt)

GGGAGACCCAAGCUGGCUAGCGUUUAAACUUAAGCUCGCCCUUCACCAUGGACUACAAAGACGAUGAC
GACAAGCUUGUGGUGGCAGCGGCGCCGAGCGCGGCCACGGCGGCCCCCAAAGUGCUACUCUUAUCU
GGCCAGCCCGCCUCCGUCGGCCGGGCGCUGCCGCUCAUGAUACCCGGUCCGCGGGAAGCAGGGUC
GGAGGCGAGCGGGACACCGCAGGCUCGCAAGCGGCAGCGCUUGGGAAUGGACACGCUGGAUCCUG
ACGAGGUUCCAGAGGUGGAGGCCAAGGGGAGUGGAGUAAGGCUGGUGGCCGGGUCUGCUGAGUCC
GCAGCACUCAGACUACGUGCACCUCUGCAGCAGGUGCAGGCCCAGUUGUCACCUCCCCAGAACAUCU
UCCCGUGAGCAAGGGCGAGGAGCUGUUCACCGGGGUGGUGCCCAUCC

XBP1/Pst (354 nt)

GGGAGACCCAAGCUGGCUAGCGUUUAAACUUAAGCUCGCCCUUCACCAUGGACUACAAAGACGAUGAC
GACAAGCUUGUGGUGGCAGCGGCGCCGAGCGCGGCCACGGCGGCCCCCAAAGUGCUACUCUUAUCU
GGCCAGCCCGCCUCCGUCGGCCGGGCGCUGCCGCUCAUGAUACCCGGUCCGCGGGAAGCAGGGUC
GGAGGCGAGCGGGACACCGCAGGCUCGCAAGCGGCAGCGCUUGGGAAUGGACACGCUGGAUCCUG
ACGAGGUUCCAGAGGUGGAGGCCAAGGGGAGUGGAGUAAGGCUGGUGGCCGGGUCUGCUGAGUCC
GCAGCACUCAGACUACGUGCACCUC

HAC1 (514 nt)

ACUUCAUGGGAGCUGCAGAUGUUUAAGACGGAAAAUGUACCAGAGUCGACGACGCUACCUGCCGUA
GACAACAACAAUUUGUUUGAUGCGGUGGCCUCGCCGUUGGCAGACCCACUCUGCGACGAUAUAGCG
GGAAACAGUCUACCCUUUGACAAUUCAAUUGAUCUUGACAAUUGGCGUAAUCCAGCCGUGAUUACGA
UGACCAGGAAACUACAGUGAACAAGAACACUAGCCCCAGCUUUUGCUUUCUGCUUUUUUUCUUUUUU
UUUUUUUUUAGUCGUGGUUCUCUGAUGGGGAGGAGCCGGUUAAAGUACCUUCAAAAGCAGAAUGC
AGGGUUAUGGAAGCUUUCUUUUUUUUCUUUUAUGCUAGUUUUUCCUGAACAAAUAGAGCCAUUCUUU
UCUUAUUACUAAGAAAUGGACGGCUUGCUUGUACUGUCCGAAGCGCAGUCAGGUUUGAAUUCAUUUG
AAUUGAAUGAUUUCUUCAUCACUUCAUGAAGACAAUCGCAAGAGGGUA

HP21

UGCACCUCUGCAGCAGGUGCA

HAC1 28-mer

GCUUGUACUGUCCGAAGCGCAGUCAGGU

XBP1 58-mer

GGGUCUGCUGAGUCCGCAGCACUCAGACUACGUGCACCUCUGCAGCAGGUGCAGGCCC

FIGURE 8

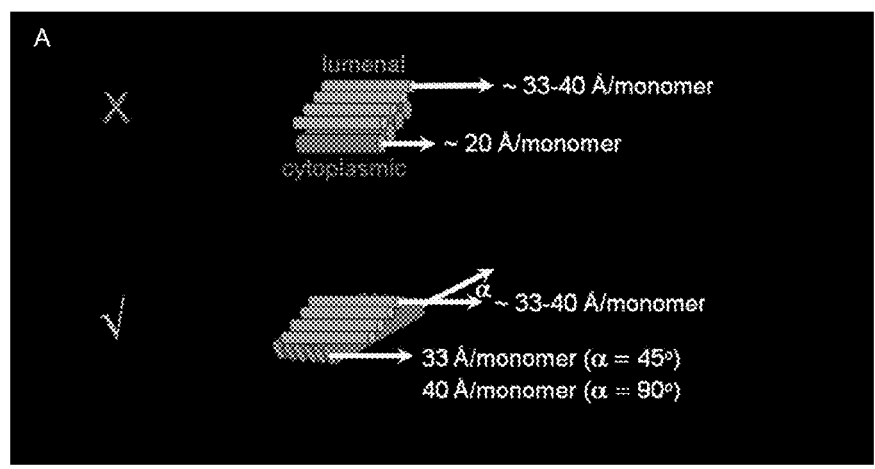
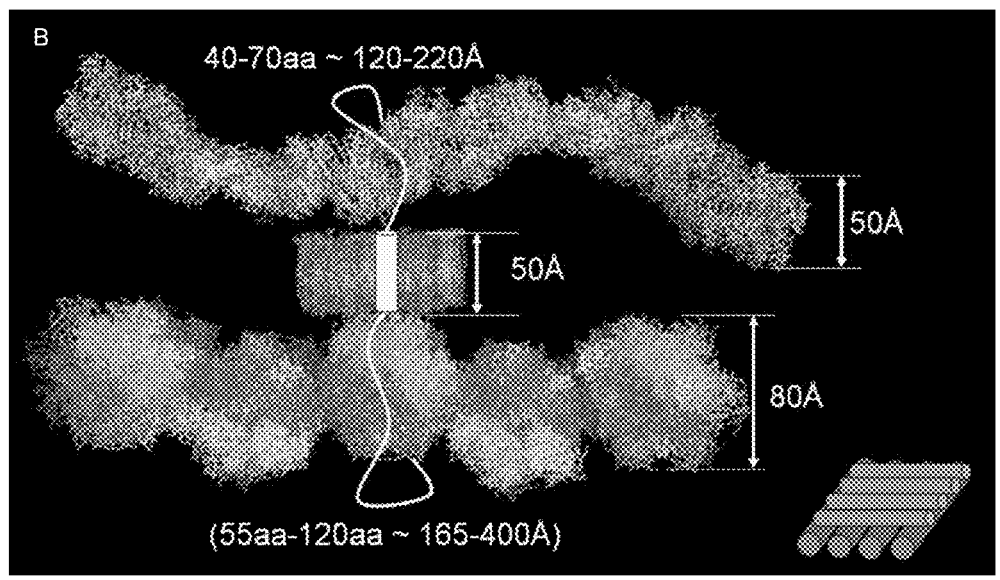
FIGURE 14

| DATA STATISTICS | |
|---|---|
| Space group | $P2_12_12$ |
| Unit cell dimensions | a=156.82, b=163.47, c=292.83 Å; a=b=g=90° |
| Resolution range, Å | 20-3.9 (4.0-3.9)* |
| I/s | 11.87 (2.86) |
| $R_{merge}(I)$ | 0.171 (0.716) |
| Completeness, % | 99.6 (99.2) |
| No of unique reflections | 69052 (4923) |
| Redundancy | 6.3 (5.8) |
| B-factors** | Protein 97 |
| | Ligand (APY) 143 |
| NCS-RESTRAINED REFINEMENT STATISTICS | |
| Resolution range, Å | 20-3.9 |
| $R/R^{free**}$ | 0.264 / 0.298 |
| RMS deviations, bond lengths | 0.004 |
| bond angles | 0.735 |
| dihedral angles | 18.27 |
| Ramachandran outliers | 0 |

*Statistics for the outer resolution shell is presented in parenthesis.
**Average B-factors were calculated from the model after grouped isotropic B-factor refinement in CNS.

FIGURE 15

| | Wild type | Kinase-dead |
|---|---|---|
| N-terminus | PEKKKRKRGSRGGKKGRKSR | PEKKKRKRGSRGGKKGRKSR |
| N-lobe | IIHR | LQK, IIHR |
| Activation loop | LDSGQSSFRTNLNNPSGT | |
| αEF-αF | SGWRAPELLEESNNLQCQVET EHSSSR | |
| C-lobe | LTR, VLR, SK, YR, ALR, EFLYS | LTR, VLR, SK, YR, ALR, EFLYS |

FIGURE 16

METHODS AND COMPOSITIONS FOR MODULATING IRE1, SRC, AND ABL ACTIVITY

CROSS-REFERENCES TO RELATED APPLICATIONS

This application is a National Stage Entry of PCT/US2009/056993, filed Sep. 15, 2009, which claims the benefit of U.S. Provisional Patent Application No. 61/097,173 filed Sep. 15, 2008, which is incorporated herein by reference in its entirety and for all purposes.

STATEMENT AS TO RIGHTS TO INVENTIONS MADE UNDER FEDERALLY SPONSORED RESEARCH AND DEVELOPMENT

The present invention was supported by a grant from the National Institutes of Health (GM60641) and by U.S. Army Medical Research and Materiel Command grant contract No. W81XWH-06-1-0383. The Government has certain rights to the invention.

BACKGROUND OF THE INVENTION

Approximately one-third of all the proteins in eukaryotes enter the ER for post-translational processing and folding. The quality of protein folding is monitored by the ER membrane-resident kinase-ribonuclease Ire1, which is activated by misfolded proteins. Ire1 initiates a non-spliceosomal cytoplasmic splicing reaction of transcription factor encoding mRNA initiating a genome-scale transcriptional program termed unfolded protein response (UPR). Translation of the spliced mRNA yields a UPR-specific transcription factor, termed Hac1 (Cox, J. S. et al., Cell 87:391-404 (1996)) in yeasts and Xbp1 (Yoshida, H. et al., Cell 107:881-91 (2001)) in metazoans, that activates genes involved in protein biogenesis and restores protein folding in the ER. The UPR activates in cancers (Koong, A. C. et al., Cancer Biol Ther 5 (2006); Ma, Y. et al., Nat Rev Cancer 4:966-77 (2004)), in Alzheimer's disease (Kudo, T. et al. Ann NY Acad Sci 977:349-55 (2002)), and in a variety of other cellular anomalies (Zheng, Y. et al. J Microbiol 43:529-36 (2005); Naidoo, N. et al., J Neurochem 92:1150-7 (2005); Doody, G. M. et al., Eur J Immunol 36:1572-82 (2006)), suggesting numerous possible links between abnormal Ire1 activation and cellular dysfunctions.

During the UPR, the ER-lumenal domain (LD) acts as a sensor of unfolded proteins and promotes lateral self-association of Ire1 in the plane of the ER membrane (FIG. 1A). Notably, the purified LD crystallizes as an oligomer that has two distinct crystallographic interfaces. Ire1 surface residues on both interfaces contribute to Ire1 activation in vivo (Credle, J. J. et al., Proc Natl Acad Sci USA 102:18773-84 (2005)). This finding explains an early observation of oligomerization of Ire1 during the UPR (Shamu, C. E. et al., Embo J 15:3028-39 (1996)) and provides a first structural rationalization of Ire1 organization in UPR-induced foci that can be observed by life-cell imaging (Kimata, Y. et al. J Cell Biol 179:75-86 (2007)) (Aragon et al., 2008). It has been proposed that oligomerization of the LD would increase the local concentration of the kinase-RNase domains of Ire1 on the cytosolic side of the ER membrane and activate the enzymatic domains by dimerization (Credle, J. J. et al., Proc Natl Acad Sci USA 102:18773-84 (2005)). This mechanism of activation parallels that for many well-understood cell surface signaling receptors. Ligand-induced dimerization of epithelial growth factor receptors (EGFR) (Zhang, X. et al., Cell 125:1137-49 (2006)), for example, activates the kinase domains by inducing conformational changes that include opening of the N- and the C-lobes of the kinase and rearrangement of the activation loop and the highly conserved αC helix (Zhang, X. et al., Cell 125:1137-49 (2006)). In addition to self-association, activation of Ire1 involves autophosphorylation and binding of ADP as a co-factor. Both of these events are thought to facilitate a conformational change that activates the RNase (Papa, F. R. et al., Science 302:1533-7 (2003); Gonzalez, T. N. et al., Methods Mol Biol 160:25-36 (2001)).

A crystal structure of the Ire1 kinase-RNase domain has been reported (Lee, K. P. et al., Cell 132:89-100 (2008)). The structure revealed a two-fold symmetric dimer with a back-to-back arrangement of the kinase domains, compactly attached to an RNase dimer with two independent active sites. The structure is well ordered except for the activation loop, the loop following the αD helix of the kinase domain, and a functionally important and apparently highly dynamic loop of the RNase domain. The back-to-back arrangement of the kinases in the dimer is unexpected because it positions the phosphorylation sites in the activation loops 43-48 Å away from the active site of the partnering molecule in the dimer. This arrangement does not appear productive for the trans-autophosphorylation of Ire1 observed in vivo (Shamu, C. E. et al., Embo J 15:3028-39 (1996)) and in vitro (Lee, K. P. et al., Cell 132:89-100 (2008)). The dimerization of the RNase domains has been proposed to allow recognition of the conserved tandem stem-loops comprising the splice sites in HAC1/XBP1 mRNA (Lee, K. P. et al., Cell 132:89-100 (2008)) (FIG. 1B).

The association of ER stress with diverse human diseases, such as cancer, diabetes, proteinopathies, and viral infections, provides reasoning to alter pathogenesis by manipulating the UPR. For example, in cystic fibrosis, it would be beneficial to increase protein folding capacity to produce more chloride channels displayed on the cell surface. On the other hand, in diabetes, pancreatic islet cells die of UPR induced apoptosis, and the Ire1 branch of the UPR has been shown to be cyto-protective. In neurodegenerative diseases and other protein folding diseases, such as retinitis pigmentosa leading to blindness, cells die of UPR-induced apoptosis. The same concepts apply to many other diseases in which the UPR has been implicated.

The present invention provides unanticipated means to pharmacologically modulate (e.g., increase or decrease to varying degrees) the capacity of cells to fold proteins and prevent UPR-induced cell death. The first small molecule capable of modulating wild type Ire1 and its mode of action are presented. Furthermore, a robust and highly efficient assay to screen for target and mode of action of Ire1 modulators together with means to screen for new ones is provided.

BRIEF SUMMARY OF THE INVENTION

Disclosed herein are Ire1 activators having the formula:

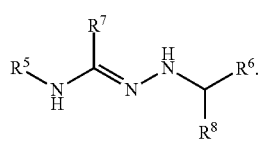

I

In Formula I, $R^5$, $R^6$, $R^7$, and $R^8$ are independently hydrogen, halogen, —CN, —NO, —NO$_2$, —NR$^{15}$R$^{16}$, —OR$^{17}$, —COOR$^{18}$, —SR$^{19}$, —COR$^{20}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^6$ and $R^7$ are optionally joined to form a substituted or unsubstituted heterocycloalkyl or substituted or unsubstituted heteroaryl. $R^{15}$, $R^{16}$, $R^{17}$, $R^{18}$, $R^{19}$ and $R^{20}$ are independently $R^{30}$-substituted or unsubstituted alkyl, $R^{30}$-substituted or unsubstituted heteroalkyl, $R^{30}$-substituted or unsubstituted cycloalkyl, $R^{30}$-substituted or unsubstituted heterocycloalkyl, $R^{30}$-substituted or unsubstituted aryl, or $R^{30}$-substituted or unsubstituted heteroaryl. $R^{30}$ is independently halogen, —CN, —CF$_3$, —OH, —NH$_2$, —SO$_2$, —COOH, $R^{31}$-substituted or unsubstituted alkyl, $R^{31}$-substituted or unsubstituted heteroalkyl, $R^{31}$-substituted or unsubstituted cycloalkyl, $R^{31}$-substituted or unsubstituted heterocycloalkyl, $R^{31}$-substituted or unsubstituted aryl, or $R^{31}$-substituted or unsubstituted heteroaryl. $R^{31}$ is independently halogen, —CN, —CF$_3$, —OH, —NH$_2$, —SO$_2$, —COOH, unsubstituted alkyl, unsubstituted heteroalkyl, unsubstituted cycloalkyl, unsubstituted heterocycloalkyl, unsubstituted aryl, or unsubstituted heteroaryl.

In another aspect, a method of modulating Ire1 activity in a cell is provided. The method includes contacting the cell with an effective amount of an Ire1 modulator as described herein or an effective amount of sunitinib.

In another aspect, a method of treating a disease caused by abnormal Ire1 activity in a subject in need of such treatment is provided. The method includes administering to the subject a therapeutically effective amount of an Ire1 modulator as described herein or a therapeutically effective amount of sunitinib.

In another aspect, a method of detecting Ire1 activating activity in a test compound is provided. The method includes contacting a test compound with a plurality of non-oligomerized Ire1 proteins in a solution. Oligomerization of the plurality of Ire1 protein is then detected thereby identifying Ire1 modulating activity in the test compound.

In another aspect, a method of detecting Ire1 deactivating activity in a test compound is provided. The method includes contacting a test compound with a plurality of oligomerized Ire1 proteins in a solution. Separation of the plurality of oligomerized Ire1 proteins thereby forming a plurality of non-oligomerized Ire1 proteins is then detected thereby identifying Ire1 deactivating activity in the test compound.

In another aspect, a method of modulating the activity of a Src tyrosine kinase is provided. The method includes contacting the Src tyrosine kinase (e.g., in a cell) with an effective amount of a modulator as described herein.

In yet another aspect, a method of modulating the activity of an Abl tyrosine kinase is provided. The method includes contacting the Abl tyrosine kinase (e.g., in a cell) with an effective amount of a modulator as described herein.

In another aspect, methods and compounds substantially as described herein are provided.

BRIEF DESCRIPTION OF THE DRAWINGS

FIG. 7. Sequences of protein constructs used. Overview of the Ire1 constructs. Legend: Pro-Ire1KR32 (SEQ ID NO:1); Ire1KR24 (SEQ ID NO:1, residues 10-476); Ire1KR (SEQ ID NO:1, residues 34-476).

FIG. 8. RNA substrates studied with intron sequences underlined. Legend: XBP1 (443 nt) (SEQ ID NO:2); XBP1/Pst (354 nt) (SEQ ID NO:3); HAC1 (514 nt) (SEQ ID NO:4); HP21 (SEQ ID NO:5); HAC1 28-mer (SEQ ID NO:6); XBP1 58-mer (SEQ ID NO:7).

FIG. 14. A model architecture of the Ire1 foci in vivo. A. Comparison of the monomer packing density along the filament axis in the crystal structures of the lumenal domain (PDB ID 2be1) and the cytoplasmic domain (current structure) of Ire1. B. A filament of the oligomeric lumenal domain (top), a modeled membrane and several copies of the oligomeric cytoplasmic domain (oriented as in FIG. 4A, side view) are shown.

FIG. 15. Data collection and refinement statistics.

FIG. 16. Tryptic peptides absent in MALDI spectra of Ire1KR32. Legend: N-terminus Wild Type and Kinase-dead (SEQ ID NO:1, residues 1-20); N-lobe Wild type and second N-lobe Kinase-dead peptide (SEQ ID NO:1, residues 154-157); Activation loop Wild type (SEQ ID NO:1, residues 196-213); aEF-aF Wild Type (SEQ ID NO:1, residues 214-240); sixth C-lobe Wild type and Kinase-dead peptides (SEQ ID NO:1, residues 472-476).

DETAILED DESCRIPTION OF THE INVENTION

I. Abbreviations and Definitions

Figure 1:
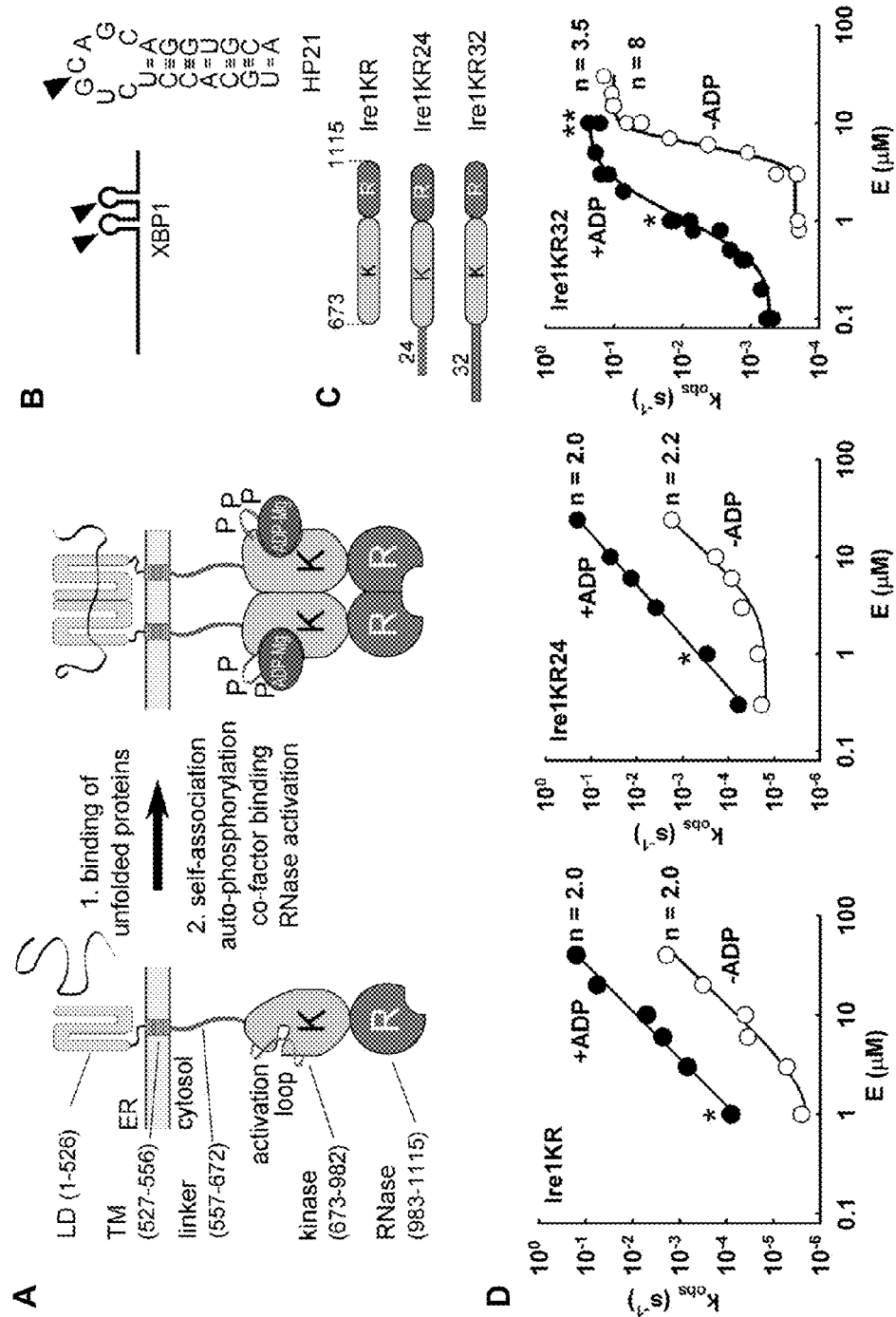
FIG. 1. Activation of Ire1 by self-association. A. Unfolded proteins in the endoplasmic reticulum (ER) bind to the lumenal domain (LD) and activate the kinase (K) and the ribonuclease (R) domains of Ire1. B. Schematic representation of Ire1 substrates used. Legend: HP21 (SEQ ID NO:5). C. Ire1 constructs used for cleavage assays and structure determination. D. Cooperative activation profiles for Ire1KR, Ire1KR24 and Ire1KR32 obtained using 5'-$^{32}$p-HP21, with (+ADP) or without (−ADP) co-factor.

The abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e. unbranched) or branched carbon chain, or combination thereof, which may be fully saturated, mono- or polyunsaturated and can include di- and multivalent radicals, having the number of carbon atoms designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkyl, as exemplified, but not limited, by —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen and sulfur atoms may optionally be oxidized and the nitrogen heteroatom may optionally be quaternized. The heteroatom(s) O, N, P and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, O—CH$_3$, —O—CH$_2$—CH$_3$, and —CN. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and "heterocycloalkylene" refer to a divalent radical derived from cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. "Arylene" and "heteroarylene" refers to a divalent radical derived from a aryl and heteroaryl, respectively. A "fused ring" refers a ring system with two or more rings having at least one bond and two atoms in common. Thus, a "fused ring aryl" and a "fused ring heteroaryl" refer to ring systems having at least one aryl and heteroaryl, respectively, that share at least one bond and two atoms in common with another ring.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo" as used herein means an oxygen that is double bonded to a carbon atom.

The term "alkylsulfonyl" as used herein means a moiety having the formula —S($O_2$)—R', where R' is an alkyl group as defined above. R' may have a specified number of carbons (e.g. "$C_1$-$C_4$ alkylsulfonyl").

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R"', —OC(O)R', —C(O)R', —$CO_2$R', —CONR'R", —OC(O)NR'R", —NR"C(O)R', —NR'—C(O) NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —$NO_2$ in a number ranging from zero to (2 m'+1), where m' is the total number of carbon atoms in such radical. R', R", R"' and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: halogen, —OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C (NR'R"R"')=NR"", —NR—C(NR'R")=NR"', —S(O)R', —S(O)$_2$R', —S(O)$_2$NR'R", —NRSO$_2$R', —CN and —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R"' and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R", R"' and R"" groups when more than one of these groups is present.

Two of the substituents on adjacent atoms of the aryl or heteroaryl ring may optionally form a ring of the formula —T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-($CH_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"')$_d$—, where s and d are independently integers of from 0 to 3, and X' is —O—, —NR'—, —S—, —S(O)—, —S(O)$_2$—, or —S(O)$_2$NR'—. The substituents R, R', R" and R"' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

A "substituent group," as used herein, means a group selected from the following moieties:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and each substituted or unsubstituted heterocycloalkyl is a substituted or unsubstituted 3 to 7 membered heterocycloalkyl.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

Thus, the compounds of the present invention may exist as salts with pharmaceutically acceptable acids. The present invention includes such salts. Examples of such salts include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, tautomers, geometric isomers and individual isomers are encompassed within the scope of the present invention. The compounds of the present invention do not include those which are known in the art to be too unstable to synthesize and/or isolate.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14

($^{14}$C). All isotopic variations of the compounds of the present invention, whether radioactive or not, are encompassed within the scope of the present invention.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

"Methods of treating a disease," as used herein, refers to methods of treating a disease state, a condition caused by a disease state, or disease symptoms. The term "treating," and conjugations thereof, include prevention of a disease.

"Sunitinib" is N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide and pharmaceutically acceptable salts thereof (e.g. CAS number 341031-54-7).

A "peptide" refers to a polymer in which the monomers are amino acids and are joined together through amide bonds, alternatively referred to as a "polypeptide" or "peptide." The terms "protein" encompasses polypeptides, proteins. Unnatural amino acids, for example, β-alanine, phenylglycine and homoarginine are also included under this definition. Amino acids that are not gene-encoded may also be used in the present invention. Furthermore, amino acids that have been modified to include reactive groups may also be used in the invention. All of the amino acids used in the present invention may be either the D- or L-isomer. The L-isomers are generally preferred. In addition, other peptidomimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983). Thus, an Ire1 protein (also referred to herein as simply "Ire1") includes recombinant Ire1 protein as well as copies of the same Ire1 protein or versions from different sources (e.g. human Ire1, mouse Ire1, yeast Ire1). Where Ire1 proteins are oligomerized, the Ire1 proteins forming the oligomer may be from the same or different sources.

II. Modulators

Disclosed herein are Ire1 modulators having the formula:

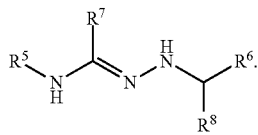

I

In Formula I, $R^5$, $R^6$, $R^7$, and $R^8$ are independently hydrogen, halogen, —CN, —NO, —NO$_2$, —NR$^{15}$R$^{16}$, —OR$^{17}$, —COOR$^{18}$, —SR$^{19}$, —COR$^{20}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^6$ and $R^7$ are optionally joined to form a substituted or unsubstituted heterocycloalkyl or substituted or unsubstituted heteroaryl.

In some embodiments, $R^5$, $R^6$, $R^7$, and $R^8$ are independently hydrogen, halogen, —CN, —NO, —NO$_2$, —NR$^{15}$R$^{16}$, —OR$^{17}$, —COOR$^{18}$, —SR$^{19}$, —COR$^{20}$, R$^{26}$-substituted or unsubstituted alkyl, R$^{26}$-substituted or unsubstituted heteroalkyl, R$^{26}$-substituted or unsubstituted cycloalkyl, R$^{26}$-substituted or unsubstituted heterocycloalkyl, R$^{26}$-substituted or unsubstituted aryl, or R$^{26}$-substituted or unsubstituted heteroaryl. R$^{26}$ is independently halogen, —CN, —CF$_3$, —OH, —NH$_2$, —SO$_2$, —COOH, R$^{27}$-substituted or unsubstituted alkyl, R$^{27}$-substituted or unsubstituted heteroalkyl, R$^{27}$-substituted or unsubstituted cycloalkyl, R$^{27}$-substituted or unsubstituted heterocycloalkyl, R$^{27}$-substituted or unsubstituted aryl, or R$^{27}$-substituted or unsubstituted heteroaryl.

In some embodiments, $R^6$ and $R^7$ are joined to form a substituted or unsubstituted heterocycloalkyl or substituted or unsubstituted heteroaryl. For example, $R^6$ and $R^7$ may be joined together to form a substituted or unsubstituted pyrazole, or substituted or unsubstituted triazole. In some embodiments, $R^6$ and $R^7$ are joined to form a substituted or unsubstituted pyrazole. In some embodiments, $R^6$ and $R^7$ are joined to form an R$^{28}$-substituted or unsubstituted heterocycloalkyl or R$^{28}$-substituted or unsubstituted heteroaryl. R$^{28}$ is independently halogen, —CN, —CF$_3$, —OH, —NH$_2$, —SO$_2$, —COOH, R$^{29}$-substituted or unsubstituted alkyl, R$^{29}$-substituted or unsubstituted heteroalkyl, R$^{29}$-substituted or unsubstituted cycloalkyl, R$^{29}$-substituted or unsubstituted heterocycloalkyl, R$^{29}$-substituted or unsubstituted aryl, or R$^{29}$-substituted or unsubstituted heteroaryl.

In some embodiments, $R^5$ is substituted or unsubstituted cycloalkyl, substituted or unsubstituted heterocycloalkyl, substituted or unsubstituted aryl, or substituted or unsubstituted heteroaryl. In some embodiments, $R^5$ is substituted or unsubstituted heteroaryl.

In some embodiments, $R^5$ is substituted or unsubstituted pyrazolyl, substituted or unsubstituted furanyl, substituted or unsubstituted imidazolyl, substituted or unsubstituted isoxazolyl, substituted or unsubstituted oxadiazolyl, substituted or unsubstituted oxazolyl, substituted or unsubstituted pyrrolyl, substituted or unsubstituted pyridyl, substituted or unsubstituted pyrimidyl, substituted or unsubstituted pyridazinyl, substituted or unsubstituted thiazolyl, substituted or unsubstituted triazolyl, substituted or unsubstituted thienyl, substituted or unsubstituted dihydrothieno-pyrazolyl, substituted or unsubstituted thianaphthenyl, substituted or unsubstituted carbazolyl, substituted or unsubstituted benzimidazolyl, substituted or unsubstituted benzothienyl, substituted or unsubstituted benzofuranyl, substituted or unsubstituted indolyl, substituted or unsubstituted quinolinyl, substituted or unsubstituted quinazolinyl, substituted or unsubstituted benzotriazolyl, substituted or unsubstituted benzothiazolyl, substituted or unsubstituted benzooxazolyl, substituted or unsubstituted benzimidazolyl, substituted or unsubstituted isoquinolinyl, substituted or unsubstituted isoindolyl, substituted or unsubstituted acridinyl, substituted or unsubstituted benzoisazolyl, or substituted or unsubstituted dimethylhydantoin. In some embodiments, $R^5$ is a five- or six-membered R$^{26}$-substituted or unsubstituted nitrogen-containing heteroaryl. In one embodiment, $R^5$ may be, for example, R$^{26}$-substituted or unsubstituted pyrimidyl or R$^{26}$-substituted or unsubstituted quinazolinyl.

$R^{15}$, $R^{16}$, $R^{17}$, $R^{18}$, $R^{19}$ and $R^{20}$ are independently R$^{30}$-substituted or unsubstituted alkyl, R$^{30}$-substituted or unsubstituted heteroalkyl, R$^{30}$-substituted or unsubstituted cycloalkyl, R$^{30}$-substituted or unsubstituted heterocycloalkyl, R$^{30}$-substituted or unsubstituted aryl, or R$^{30}$-substituted or unsubstituted heteroaryl. R$^{30}$ is independently halogen, —CN, —CF$_3$, —OH, —NH$_2$, —SO$_2$, —COOH, R$^{31}$-substituted or unsubstituted alkyl, R$^{31}$-substituted or unsubstituted heteroalkyl, $R^{31}$-substituted or unsubstituted cycloalkyl, $R^{31}$-substituted or unsubstituted heterocycloalkyl, $R^{31}$-substituted or unsubstituted aryl, or $R^{31}$-substituted or unsubstituted heteroaryl.

$R^{27}$, $R^{29}$, and $R^{31}$ are independently halogen, —CN, —$CF_3$, —OH, —$NH_2$, —$SO_2$, —COOH, unsubstituted alkyl, unsubstituted heteroalkyl, unsubstituted cycloalkyl, unsubstituted heterocycloalkyl, unsubstituted aryl, or unsubstituted heteroaryl.

In some embodiments, the Ire1 modulator has the formula:

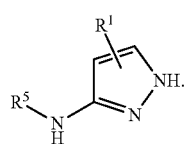

II

Without being bound by theory, it is believed that the above-illustrated 3-nitrogen motif is responsible for the Ire1 modulating effect.

In Formula II, $R^5$ is as defined above in the description of Formula I.

In Formula II, $R^1$ is hydrogen, halogen, —CN, —NO, —$NO_2$, —$NR^9R^{10}$, —$OR^{11}$, —$COOR^{12}$, —$SR^{13}$, —$COR^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^1$ is $R^{32}$-substituted or unsubstituted alkyl, $R^{32}$-substituted or unsubstituted heteroalkyl, $R^{32}$-substituted or unsubstituted cycloalkyl, $R^{32}$-substituted or unsubstituted heterocycloalkyl, $R^{32}$-substituted or unsubstituted aryl, or $R^{32}$-substituted or unsubstituted heteroaryl. $R^{32}$ is halogen, —CN, —$CF_3$, —OH, —$NH_2$, —$SO_2$, —COOH, $R^{33}$-substituted or unsubstituted alkyl, $R^{33}$-substituted or unsubstituted heteroalkyl, $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl.

In some embodiments, $R^1$ is $R^{32}$-substituted or unsubstituted $C_1$-$C_{10}$ alkyl, $R^{32}$-substituted or unsubstituted 2 to 10 membered heteroalkyl, $R^{32}$-substituted or unsubstituted $C_3$-$C_8$ cycloalkyl, $R^{32}$-substituted or unsubstituted 3 to 8 membered heterocycloalkyl, $R^{32}$-substituted or unsubstituted aryl, $R^{32}$-substituted or unsubstituted heteroaryl. In other embodiments, $R^1$ is $R^{32}$-substituted or unsubstituted $C_1$-$C_5$ alkyl, $R^{32}$-substituted or unsubstituted 2 to 5 membered heteroalkyl, $R^{32}$-substituted or unsubstituted $C_3$-$C_6$ cycloalkyl, $R^{32}$-substituted or unsubstituted 5 or 6 membered heterocycloalkyl, $R^{32}$-substituted or unsubstituted aryl, $R^{32}$-substituted or unsubstituted heteroaryl. In some embodiments, $R^1$ is unsubstituted $C_1$-$C_5$ alkyl or unsubstituted $C_3$-$C_6$ cycloalkyl. In some embodiments, $R^1$ is unsubstituted $C_3$-$C_6$ cycloalkyl such as, e.g., cyclopropyl. In other embodiments, $R^1$ is a $R^{32}$-substituted or unsubstituted 5 or 6 membered heterocycloalkyl, such as, e.g., an unsubstituted thienyl or a $C_1$-$C_4$-substituted thienyl.

$R^9$, $R^{10}$, $R^{11}$, $R^{12}$, $R^{13}$, and $R^{14}$ are independently hydrogen, $R^{34}$-substituted or unsubstituted alkyl, $R^{34}$-substituted or unsubstituted heteroalkyl, $R^{34}$-substituted or unsubstituted cycloalkyl, $R^{34}$-substituted or unsubstituted heterocycloalkyl, $R^{34}$-substituted or unsubstituted aryl, or $R^{34}$-substituted or unsubstituted heteroaryl. $R^{34}$ is independently halogen, —CN, —$CF_3$, —OH, —$NH_2$, —$SO_2$, —COOH, $R^{35}$-substituted or unsubstituted alkyl, $R^{35}$-substituted or unsubstituted heteroalkyl, $R^{35}$-substituted or unsubstituted cycloalkyl, $R^{35}$-substituted or unsubstituted heterocycloalkyl, $R^{35}$-substituted or unsubstituted aryl, or $R^{35}$-substituted or unsubstituted heteroaryl.

$R^{33}$ and $R^{35}$ are independently halogen, —CN, —$CF_3$, —OH, —$NH_2$, —$SO_2$, —COOH, unsubstituted alkyl, unsubstituted heteroalkyl, unsubstituted cycloalkyl, unsubstituted heterocycloalkyl, unsubstituted aryl, or unsubstituted heteroaryl.

In other embodiments, the Ire1 modulator has the formula:

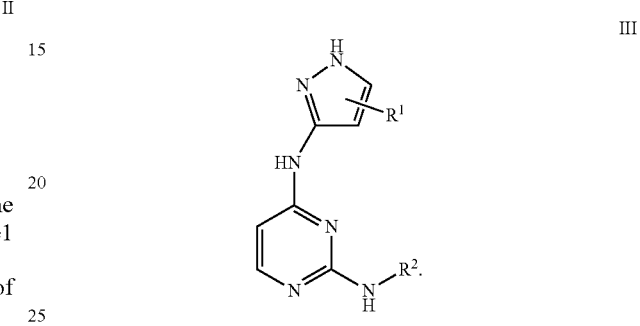

III

In Formula III, $R^1$ is as defined above for $R^1$ in the description of Formula II.

Similarly, $R^2$ is independently hydrogen, halogen, —CN, —NO, —$NO_2$, —$NR^9R^{10}$, —$OR^{11}$, —$COOR^{12}$, —$SR^{13}$, —$COR^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^9$, $R^{10}$, $R^{11}$, $R^{12}$, $R^{13}$, and $R^{14}$ are independently as defined above in the description of Formula II.

$R^2$ may be substituted or unsubstituted $C_1$-$C_{10}$ alkyl, substituted or unsubstituted 2 to 10 membered heteroalkyl, substituted or unsubstituted $C_3$-$C_8$ cycloalkyl, substituted or unsubstituted 3 to 8 membered heterocycloalkyl, substituted or unsubstituted aryl, substituted or unsubstituted heteroaryl.

In some embodiments, $R^2$ is $R^3$-substituted or unsubstituted aryl or $R^3$-substituted or unsubstituted heteroaryl. For example, $R^2$ can be $R^3$-substituted or unsubstituted phenyl. $R^3$ is halogen, —CN, —$CF_3$, —OH, —$NH_2$, —$SO_2$, —COOH, —SH, —$NO_2$, oxo, —$NHR^4$, $R^4$-substituted or unsubstituted alkyl, $R^4$-substituted or unsubstituted heteroalkyl, $R^4$-substituted or unsubstituted cycloalkyl, $R^4$-substituted or unsubstituted heterocycloalkyl, $R^4$-substituted or unsubstituted aryl, or $R^4$-substituted or unsubstituted heteroaryl. $R^4$ is halogen, —CN, —$CF_3$, —OH, —$NH_2$, —$SO_2$, —COOH, —SH, —$NO_2$, oxo, unsubstituted alkyl, unsubstituted heteroalkyl, unsubstituted cycloalkyl, unsubstituted heterocycloalkyl, unsubstituted aryl, or unsubstituted heteroaryl.

In other embodiments, $R^2$ is substituted or unsubstituted phenyl, substituted or unsubstituted pyrazolyl, substituted or unsubstituted furanyl, substituted or unsubstituted imidazolyl, substituted or unsubstituted isoxazolyl, substituted or unsubstituted oxadiazolyl, substituted or unsubstituted oxazolyl, substituted or unsubstituted pyrrolyl, substituted or unsubstituted pyridyl, substituted or unsubstituted pyrimidyl, substituted or unsubstituted pyridazinyl, substituted or unsubstituted thiazolyl, substituted or unsubstituted triazolyl, substituted or unsubstituted thienyl, substituted or unsubstituted dihydrothieno-pyrazolyl, substituted or unsubstituted thianaphthenyl, substituted or unsubstituted carbazolyl, substituted or unsubstituted benzimidazolyl, substituted or unsubstituted benzothienyl, substituted or unsubstituted benzofuranyl, substituted or unsubstituted indolyl, substituted or unsubstituted quinolinyl, substituted or unsubstituted benzotriazolyl, substituted or unsubstituted benzothiazolyl, substituted or unsubstituted benzooxazolyl, substituted or unsubstituted benzimidazolyl, substituted or unsubstituted isoquinolinyl, substituted or unsubstituted isoindolyl, substituted or unsubstituted acridinyl, substituted or unsubstituted benzoisazolyl, or substituted or unsubstituted dimethylhydantoin. $R^2$ may also be substituted or unsubstituted phenyl, or substituted or unsubstituted benzimidazolyl. In other embodiments, $R^2$ is unsubstituted phenyl or unsubstituted benzimidazolyl. In some embodiments $R^2$ is a substituted or unsubstituted fused ring aryl or substituted or unsubstituted fused ring heteroaryl, e.g., a substituted or unsubstituted benzimidazolyl or substituted or unsubstituted benzothiazolyl.

In other embodiments, the Ire1 modulator has the formula:

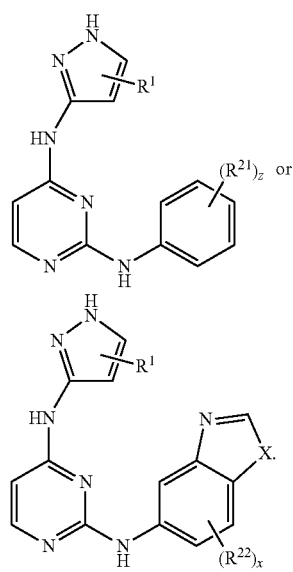

IV

V

In Formulae IV and V, $R^1$ is as defined above in the description of Formula II.

Similarly, $R^{21}$ and $R^{22}$ are independently hydrogen, halogen, —CN, —NO, —NO$_2$, —NR$^9$R$^{10}$, —OR$^{11}$, —COOR$^{12}$, —SR$^{13}$, —COR$^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^{21}$ and $R^{22}$ are independently halogen, —CN, —NO, —NO$_2$, —NR$^9$R$^{10}$, —OR$^{11}$, —COOR$^{12}$, —SR$^{13}$, —COR$^{14}$, $R^{25}$-substituted or unsubstituted alkyl (e.g., $C_1$-$C_{10}$ alkyl), $R^{25}$-substituted or unsubstituted heteroalkyl (e.g., 2-10 members), $R^{25}$-substituted or unsubstituted cycloalkyl, $R^{25}$-substituted or unsubstituted heterocycloalkyl, $R^{25}$-substituted or unsubstituted aryl, or $R^{25}$-substituted or unsubstituted heteroaryl.

$R^9$, $R^{10}$, $R^{11}$, $R^{12}$, $R^{13}$, and $R^{14}$ are independently as defined above in the description of Formula II.

$R^{25}$ is halogen, —CN, —CF$_3$, —OH, —NH$_2$, —SO$_2$, —COOH, —SH, —NO, —NO$_2$, oxo, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^{25}$ is halogen, —CN, —CF$_3$, —OH, —NH$_2$, —SO$_2$, —COOH, —SH, —NO$_2$, —NO, oxo, unsubstituted alkyl, unsubstituted heteroalkyl, unsubstituted cycloalkyl, unsubstituted heterocycloalkyl, unsubstituted aryl, or unsubstituted heteroaryl.

In some embodiments, $R^{21}$ is —CN, —NO, —NO$_2$, —OH, —COOR$^{12}$, —SR$^{13}$, substituted or unsubstituted alkyl (e.g., $C_1$-$C_{10}$ alkyl), substituted or unsubstituted cycloalkyl, substituted or unsubstituted aryl, or substituted or unsubstituted heteroaryl. In other embodiments, $R^{21}$ is a $R^{25}$-substituted or unsubstituted $C_1$-$C_4$ alkyl or $R^{25}$-substituted or unsubstituted 2-4 membered heteroalkyl. In some embodiments, $R^{25}$ is —CN, —CF$_3$, —OH, or oxo. In some embodiments, $R^{21}$ is —CH$_2$—CN. In other embodiments, $R^{21}$ is —CH$_2$CH$_2$OH. In other embodiments, $R^{21}$ is —NH—CO—CH$_3$.

In Formula V, X is NH or S. In some embodiments, X is NH.

The symbols x and z are independently integers from 0 to 5. In some embodiments, x and z are independently 0 or 1. In one embodiment, z is 1. In another embodiment, x is 0.

In yet another embodiment, the Ire1 modulator has the formula:

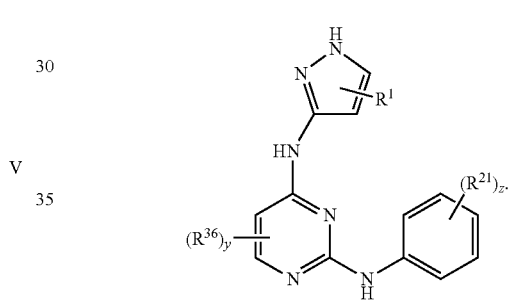

VI

In Formula VI, $R^1$, $R^{21}$, and z are as defined above in the description of Formula IV.

In some embodiments, z is more than 1, and two adjacent $R^{21}$ substituents are joined to form a substituted or unsubstituted aryl or substituted or unsubstituted heteroaryl. In one embodiment, two adjacent $R^{21}$ substituents are joined to form a substituted or unsubstituted thiazolyl or substituted or unsubstituted imidazolyl.

The symbol y is an integer from 0 to 4. In some embodiments, y is 0, 1, or 2.

$R^{36}$ is independently hydrogen, halogen, —CN, —NO, —NO$_2$, —NR$^9$R$^{10}$, —OR$^{11}$, —COOR$^{12}$, —SR$^{13}$, —COR$^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$, $R^{10}$, $R^{11}$, $R^{12}$, $R^{13}$, and $R^{14}$ are independently as defined above in the description of Formula II. In some embodiments, $R^{36}$ is a substituted or unsubstituted $C_1$-$C_{10}$ alkyl. In one embodiment, $R^{36}$ is unsubstituted $C_1$-$C_4$ alkyl, e.g., methyl.

In some embodiments, y is more than 1, and two adjacent $R^{36}$ substituents are joined to form a substituted or unsubstituted aryl or substituted or unsubstituted heteroaryl. In some embodiments, two adjacent $R^{36}$ substituents are joined to form a substituted or unsubstituted phenyl such that in one embodiment, the Ire1 modulator has the formula:

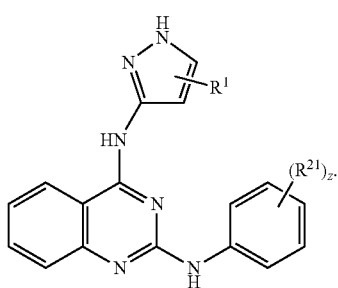

In Formula VII, $R^1$, $R^{21}$, and z are as defined above in the description of Formula VI.

In other embodiment, the Ire1 modulator has the formula:

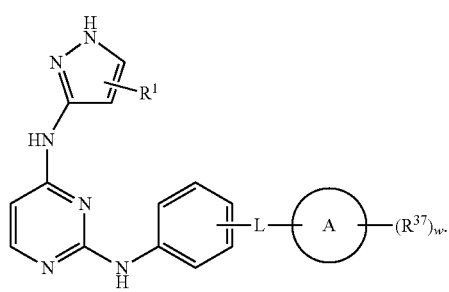

In Formula VIII, $R^1$ is as defined above in the description of Formula VI.

In Formula VIII, L is a bond, substituted or unsubstituted alkylene, substituted or unsubstituted heteroalkylene, —NH—C(O)—, or —NH—C(O)—NH—. In some embodiments, L is a bond, $R^{38}$-substituted or unsubstituted alkylene or $R^{38}$-substituted or unsubstituted heteroalkylene. $R^{38}$ is halogen, oxo, —CN, —CF$_3$, —OH, —NH$_2$, —SO$_2$, —COOH, $R^{39}$-substituted or unsubstituted alkyl, $R^{39}$-substituted or unsubstituted heteroalkyl, $R^{39}$-substituted or unsubstituted cycloalkyl, $R^{39}$-substituted or unsubstituted heterocycloalkyl, $R^{39}$-substituted or unsubstituted aryl, or $R^{39}$-substituted or unsubstituted heteroaryl. $R^{39}$ is halogen, —CN, —CF$_3$, —OH, —NH$_2$, —SO$_2$, —COOH, unsubstituted alkyl, unsubstituted heteroalkyl, unsubstituted cycloalkyl, unsubstituted heterocycloalkyl, unsubstituted aryl, or unsubstituted heteroaryl. In some embodiments, L is $R^{38}$-substituted or unsubstituted heteroalkylene where $R^{38}$ is oxo. In some embodiments, L is —NH—C(O)— or —NH—C(O)—NH—.

In Formula VIII, ring A is aryl or heteroaryl. In some embodiment, ring A is aryl, e.g., phenyl.

In Formula VIII, $R^{37}$ is halogen, —CN, —CF$_3$, —OH, —NH$_2$, —SO$_2$, —COOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^{37}$ is halogen, —CN, —CF$_3$, —OH, —NH$_2$, —SO$_2$, —COOH, $R^{40}$-substituted or unsubstituted alkyl, $R^{40}$-substituted or unsubstituted heteroalkyl, $R^{40}$-substituted or unsubstituted cycloalkyl, $R^{40}$-substituted or unsubstituted heterocycloalkyl, $R^{40}$-substituted or unsubstituted aryl, or $R^{40}$-substituted or unsubstituted heteroaryl. $R^{40}$ is halogen, —CN, —CF$_3$, —OH, —NH$_2$, —SO$_2$, —COOH, unsubstituted alkyl, unsubstituted heteroalkyl, unsubstituted cycloalkyl, unsubstituted heterocycloalkyl, unsubstituted aryl, or unsubstituted heteroaryl. In one embodiment, $R^{37}$ is substituted or unsubstituted $C_1$-$C_4$ alkyl. In one embodiment, $R^{37}$ is —CF$_3$.

The symbol w is an integer from 0 to 5. In one embodiment, w is 0 or 1. In another embodiment, w is 1.

In some embodiments of the Formulae described herein, each substituted group is substituted with at least one substituent group. More specifically, in some embodiments, each substituted alkyl, substituted heteroalkyl, substituted alkylene, substituted heteroalkylene, substituted cycloalkyl, substituted heterocycloalkyl, substituted aryl, and substituted heteroaryl described above in the compounds of the Formulae above are substituted with at least one substituent group. In other embodiments, at least one or all of these groups are substituted with at least one size-limited substituent group. Alternatively, at least one or all of these groups are substituted with at least one lower substituent group.

In other embodiments of the compounds of the Formulae above, each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkyl is a substituted or unsubstituted $C_3$-$C_8$ cycloalkyl, and each substituted or unsubstituted heterocycloalkyl is a substituted or unsubstituted 3 to 8 membered heterocycloalkyl.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkyl is a substituted or unsubstituted $C_3$-$C_7$ (e.g. $C_5$-$C_7$) cycloalkyl, and each substituted or unsubstituted heterocycloalkyl is a substituted or unsubstituted 3 to 7 (e.g. 5 to 7) membered heterocycloalkyl.

In some embodiments of the Formulae described herein, the compound can include at least two substituents that are attached to adjacent members of the base. In these embodiments, two adjacent substituents may optionally be joined to form aryl, heteroaryl, cycloalkyl, or heterocycloalkyl groups.

In another embodiments, the Ire1 modulator compound has one of the following formulae:

APY29

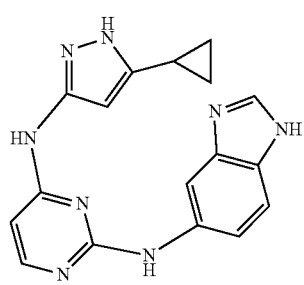

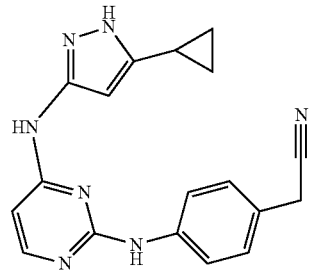
APY24
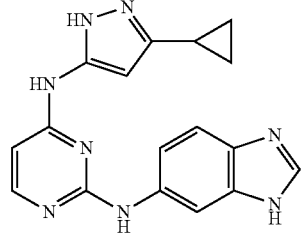
APY29
ASC29
In another embodiment, the Ire1 modulator compound has one of the following formulae:
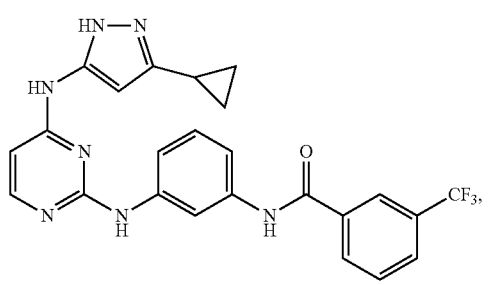
AD76
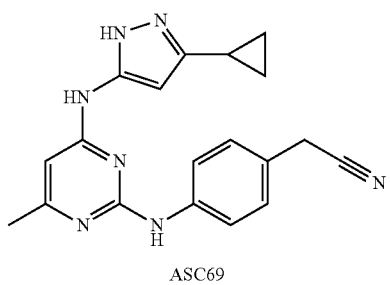
APY69
ASC69
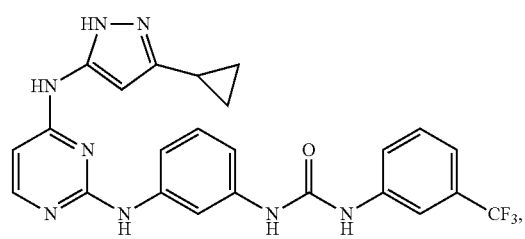
AD77
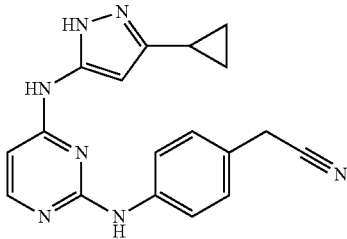
APY24
ASC24
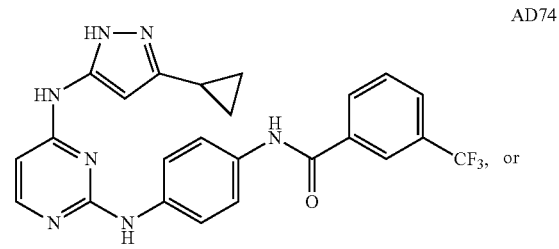
AD74 or
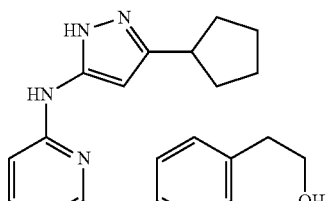
APY76
ASC 76
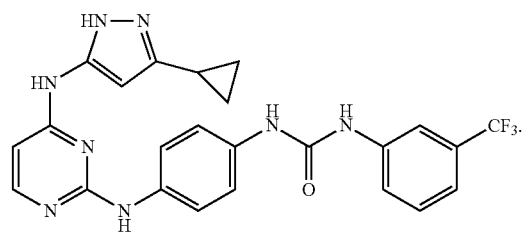
AD75
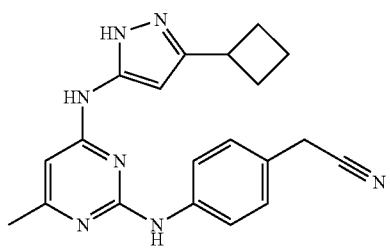
APY83
ASC 83
In one embodiment, the compound is AD75.
In another embodiments, the Ire1 modulator is a compound according to the following formulae.

-continued
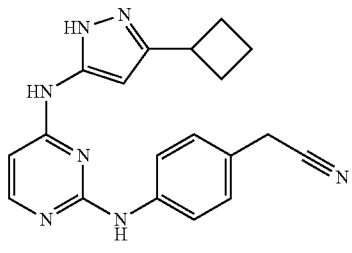
APY77
ASC 77
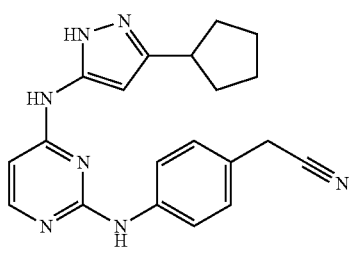
APY67
ASC67
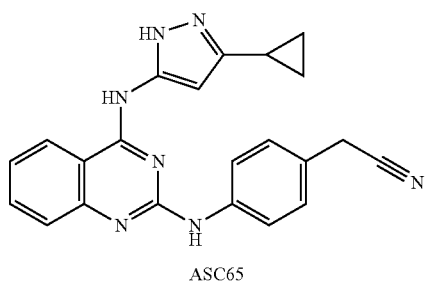
APY65
ASC65
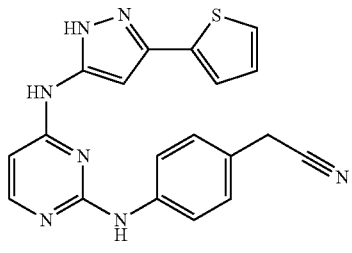
APY84
ASC 84
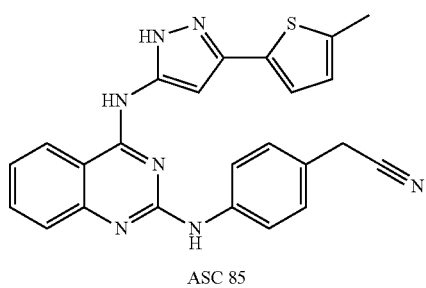
APY85
ASC 85
-continued
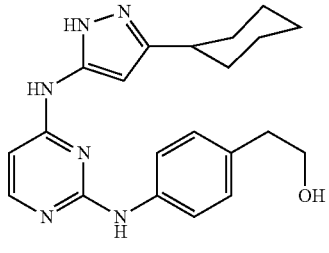
APY33
ASC33
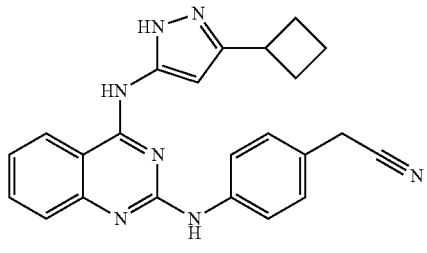
APY82
ASC 82
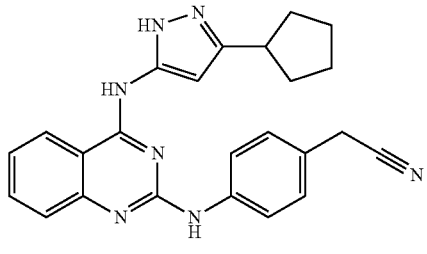
APY78
ASC 78
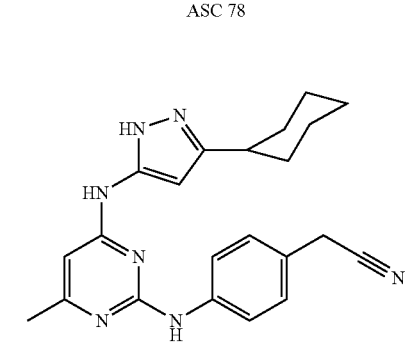
APY81
ASC 81
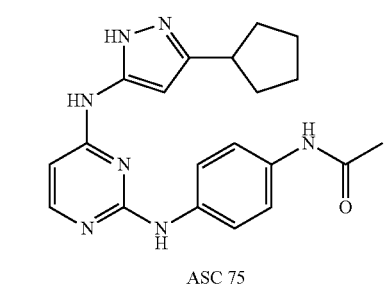
APY75
ASC 75

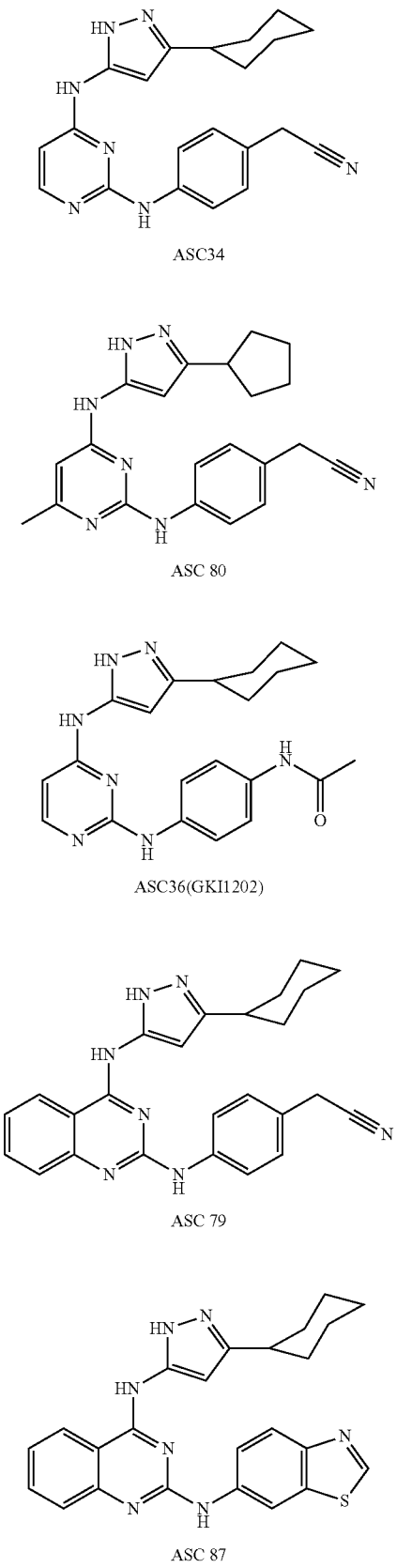
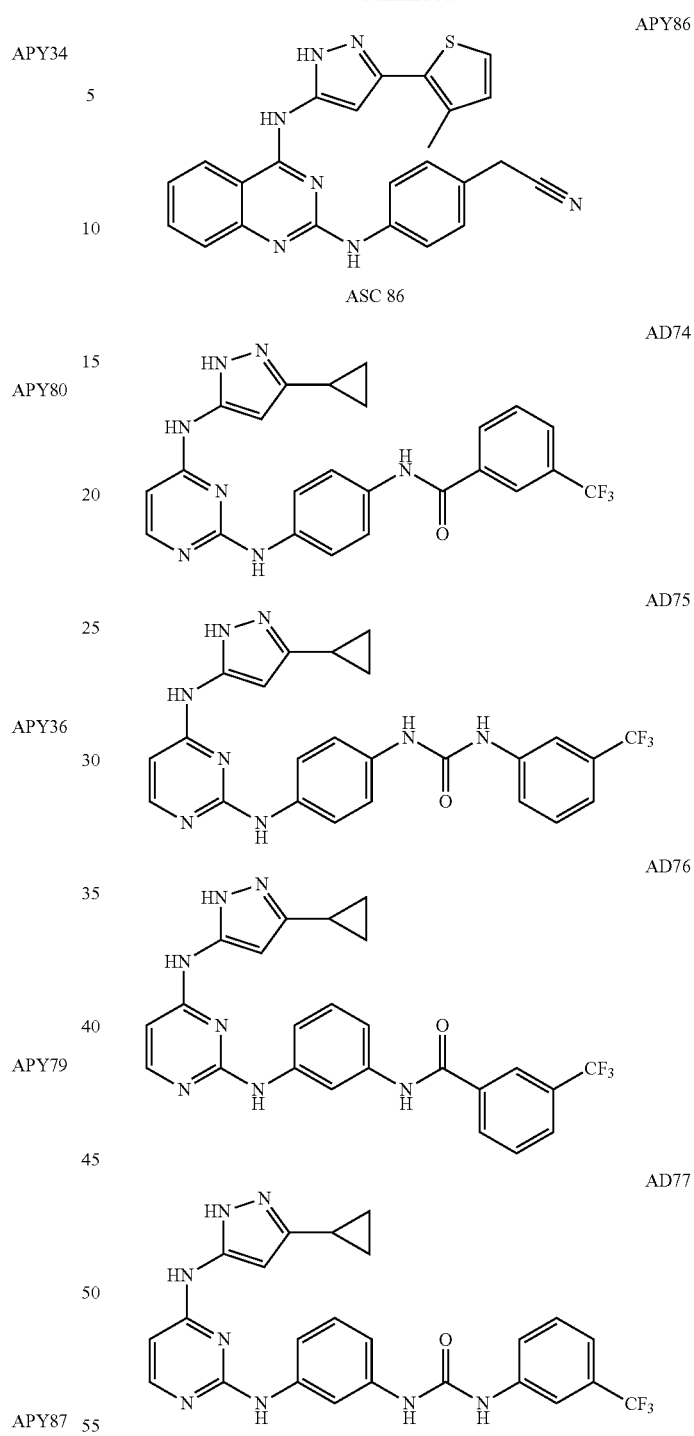

In one embodiment, the compound demonstrates significant activation of Ire1, such as compounds AD75, AD74, AD76, AD77, APY29, APY69, APY24, APY76, APY83, APY77, APY67, APY65, APY84, and APY85. In another embodiment, the compound demonstrates significant in vivo activation of Ire1, such as compound APY69, APY24, APY76, APY83, APY65, APY84, and APY82. In yet another embodiment, the compound demonstrates significant inhibition of Ire1, such as compounds APY84, APY33, APY81, APY80, APY79, and APY86.

III. Methods

In another aspect, a method of modulating Ire1 activity in a cell is provided. The method includes contacting the cell with an effective amount of an Ire1 modulator as described above (e.g. a compound of Formula I-VIII) or an effective amount of sunitinib. In some embodiments, the cell is a mammalian cell, such as a human cell. The cell may be isolated in vitro, form part of a tissue in vitro, or may form part of an organism.

Modulating Ire1 activity includes directly or indirectly affecting one or more functions of Ire1 and/or one or more downstream effects of Ire1. In other words, the function or effect of Ire1 is altered compared to the function or effect of Ire1 when the modulator is not present.

In one embodiment, the Ire1 modulator is an Ire1 inhibitor that decreases one or more of: activation of Ire1 by misfolded proteins, initiation of UPR, trans-autophosphorylation of Ire1, co-factor binding by Ire1, translation of Hac1, translation of Xbp1, and correct protein folding. For example, since Xbp1 overexpression is correlated to multiple myeloma, in some embodiments, an effective amount of Ire1 is an amount that decreases Xbp1 expression relative to the expression of Xbp1 in the absence of Ire1 inhibitor. In another embodiment, an effective amount of Ire1 inhibitor is an amount sufficient to decrease Ire1 activity in the cell to reduce UPR relative to the amount of UPR in the absence of Ire1 inhibitor.

In another embodiment, the Ire1 modulator is an Ire1 activator that increases one or more of: activation of Ire1 by misfolded proteins, initiation of UPR, trans-autophosphorylation, co-factor binding, translation of Hac1, translation of Xbp1, and corrected protein folding. Thus, an effective amount of Ire1 activator or sunitinib is an amount sufficient to increase Ire1 activity in the cell to reduce misfolded protein accumulation relative to the amount of misfolded protein accumulation in the absence of Ire1 activator or sunitinib.

In one embodiment, modulating Ire1 activity comprises direct binding of the Ire1 modulator to Ire1. In another embodiment, modulating Ire1 activity is accomplished indirectly.

Also provided herein is a method of treating a disease caused by abnormal levels of Ire1 activity in a subject in need of such treatment. The disease may be caused by an amount of Ire1 activity that is too low or too high. For example, the disease may be caused by a deficiency in Ire1 activity or by abnormally high Ire1 activity (e.g., hyperactivity of Ire1). The method includes administering to the subject a therapeutically effective amount of an Ire1 modulator as described above (e.g. a compound of Formula I-VIII) or a therapeutically effective amount of sunitinib.

Ire1 deficiency is a decreased amount of Ire1 activity compared to normal levels of Ire1 activity in a particular subject or a population of healthy subjects. The decreased amount of Ire1 activity results in excessive amounts of misfolded protein accumulation thereby causing the disease state.

Ire1 hyperactivity is an increased amount of Ire1 activity compared to normal levels of Ire1 activity in a particular subject or a population of healthy subjects. The increased amount of Ire1 activity may result in, for example, excessive amounts of cell proliferation thereby causing the disease state.

In some embodiments, the disease is associated with Ire1 deficiency. Such diseases include, but are not limited to, cystic fibrosis, retinitis pigmentosa, diabetes, or a neurodegenerative disease. The neurodegenerative disease may include Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, Huntington's disease, HIV-associated dementia, Kennedy's disease, Krabbe's disease, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoffs disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, or Tabes dorsalis.

In other embodiments, the disease is associated with abnormally high Ire1. Such diseases include, but are not limited to, cancers, inflammatory diseases, and autoimmune diseases. Exemplary cancers include, but are not limited to, breast cancer and multiple myeloma. In one embodiment, the disease is multiple myeloma. Exemplary inflammatory diseases include, but are not limited to, asthma, chronic inflammation, chronic prostatitis, glomerulonephritis, hypersensitivities, inflammatory bowel diseases, pelvic inflammatory disease; reperfusion injury, rheumatoid arthritis, transplant rejection, and vasculitis. Exemplary autoimmune diseases include, but are not limited to, XBP1-linked Crohn's disease, Coeliac disease, diabetes mellitus type 1 (IDDM), systemic lupus erythematosus (SLE), Sjögren's syndrome, Churg-Strauss Syndrome, Hashimoto's thyroiditis, Graves' disease, idiopathic thrombocytopenic purpura, and rheumatoid arthritis. In one embodiment, the diseases is XBP1-linked Crohn's disease.

The subject of treatment for the disease is typically a mammal. The mammals treated with the Ire1 modulator or sunitinib may be humans, nonhuman primates, and/or non-human mammals (e.g., rodents, canines).

In another aspect, the modulators described herein may also modulate the activity of a Src tyrosine kinase. Accordingly, a method of modulating the activity of a Src tyrosine kinase is provided. The method includes contacting the Src tyrosine kinase with an effective amount of a modulator as described above (e.g. a compound of Formula I-VIII).

In yet another aspect, the modulators described herein may also modulate the activity of an Abl tyrosine kinase. Accordingly, a method of modulating the activity of an Abl tyrosine kinase is provided. The method includes contacting the Abl tyrosine kinase with an effective amount of a modulator as described above (e.g. a compound of Formula I-VIII).

IV. Assays

The modulation of Ire1 activity may be identified by contacting a test compound with Ire1 proteins in a solution.

Oligomerization of a plurality of Ire1 protein can be detected by identifying Ire1 modulating activity in the test compound. Oligomerization of the plurality of Ire1 proteins (or oligomerized Ire1 proteins) refers to the non-covalent binding of two or more Ire1 proteins together. In some embodiments, the oligomerization is the non-covalent binding of more than 2 Ire1 proteins together. In some embodiments, the oligomerization is the non-covalent binding of about 3, 4, 5, 6, 7, 8, 9, 10, 20, 30, 40, 50, 60, 70, 80, 90 or 100 Ire1 proteins together or at least 3, 4, 5, 6, 7, 8, 9, 10, 20, 30, 40, 50, 60, 70, 80, 90 or 100 Ire1 proteins together. In other embodiments, the oligomerization is the non-covalent binding of dozens of Ire1 proteins together. The oligomerization of the Ire1 proteins is described in more detail in the Examples section below. Non-oligomerized Ire1 proteins refer to a plurality of Ire1 proteins that are not oligomerized.

In one aspect, Ire1 modulators are identified by contacting a test compound with a plurality of oligomerized Ire1 proteins in a solution. Separation of the plurality of oligomerized Ire1 proteins thereby forming a plurality of non-oligomerized Ire1 proteins is then detected thereby identifying modulation of Ire1 activity by the test compound.

Detection of oligomerization of a plurality of non-oligomerized Ire1 proteins may be achieved by any known technique. For example, detection is achieved by detecting a decrease of transparency (e.g. an increase in turbidity and light scattering) in the solution. Alternatively, a first portion of the plurality of Ire1 proteins are labeled with a donor fluorophore and a second portion of said plurality of Ire1 proteins are labeled with an acceptor fluorophore (e.g. a quencher). The oligomerization detection is achieved by detecting a change in fluorescent signal. The same techniques may be used to detect separation of the plurality of oligomerized Ire1 proteins that form a plurality of non-oligomerized Ire1 proteins. Oligomerization may also be detected by measuring the enzymatic activity of the Ire1 RNase using radioactively labeled or fluorescently labeled RNA. The RNA cleavage activity of Ire1 increases upon oligomerization or decreases upon de-oligomerization caused by the test compounds.

In some embodiments, the oligomerization is detected by monitoring the enzymatic activity (e.g. RNase or kinase) of Ire1 with the use of RNA substrates under conditions wherein oligomeric Ire1 contributes to the overall enzymatic rate. The overall enzymatic rates may be verified by the presence of the cooperative activation profiles. For example, the Hill coefficient n can be greater than 1, 2, 3, 4, 5, 6, 7, 8, 10 or more (see FIG. 1).

For example, inhibition can be achieved by binding of the compound to Ire1 in state of a monomer, dimer, or higher-order oligomer. The inhibition can be achieved due to disruption of Ire1 oligomers or dimers, altering conformation of Ire1, or competition of the inhibitor with the RNA substrate for binding to Ire1. The inhibitor can act competitively, non-competitively, uncompetitively, or in a mixed mode.

Inhibition or activation of Ire1 can be detected by measuring enzymatic activity of Ire1 in RNA cleavage assay. The RNA cleavage assays use, for example, radioactively labeled RNA, fluorescently labeled RNA, unlabeled RNA, or RNA labeled by other means. Inhibition or activation can alternatively be measured using Ire1 kinase activity assays. Inhibition or activation of Ire1 can alternatively be measured using biophysical methods such as dynamic light scattering, analytical ultracentrifugation, isothermal calorimetry, etc. that detect protein-protein or protein-ligand interactions. Inhibition or activation of Ire1 can also be measured using any suitable cell-based assays based on contacting compounds with cells or animals and monitoring the kinase activity of Ire1, monitoring the RNase activity of Ire1, or monitoring downstream effects of Ire1 activation. Downstream effects of Ire1 activation include production of spliced Hac1 or XBP1 protein, or changes involving transcriptional targets of these two proteins, or downstream changes induced by the kinase activity of Ire1. Successful modulators will affect the RNase activity of Ire1, the kinase activity of Ire1, or the oligomeric state of Ire1.

V. Pharmaceutical Compositions

In another aspect, the present invention provides pharmaceutical compositions comprising a compound of the invention (i.e., the Ire1 modulator) in combination with a pharmaceutically acceptable carrier. The pharmaceutical compositions include optical isomers, diastereomers, or pharmaceutically acceptable salts of the inhibitors disclosed herein. The compound included in the pharmaceutical composition may be covalently attached to a carrier moiety, as described above. Alternatively, the compound included in the pharmaceutical composition is not covalently linked to a carrier moiety.

A "pharmaceutically suitable carrier," as used herein refers to pharmaceutical excipients, for example, pharmaceutically or physiologically, acceptable organic, or inorganic carrier substances suitable for enteral or parenteral application that do not deleteriously react with the compound. Suitable pharmaceutically acceptable carriers include water, salt solutions (such as Ringer's solution), alcohols, oils, gelatins, carbohydrates such as lactose, amylose or starch, fatty acid esters, hydroxymethycellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention.

The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation).

The compounds of the present invention can be prepared and administered in a wide variety of oral, parenteral and topical dosage forms. Thus, the compounds of the present invention can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance, that may also act as diluents, flavoring agents, binders, preservatives, tablet disintegrating agents, or an encapsulating material.

In powders, the carrier is a finely divided solid in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampules are convenient unit dosages. The compounds of the invention can also be incorporated into liposomes or administered via transdermal pumps or patches. Pharmaceutical admixtures suitable for use in the present invention are well-known to those of skill in the art and are described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60 and 80; Pluronic F-68, F-84 and P-103; cyclodextrin; polyoxyl 35 castor oil; or other agents known to those skilled in the art. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, combinations of the foregoing, and other agents known to those skilled in the art. Such agents are typically employed at a level between about 0.01% and about 2% by weight. Determination of acceptable amounts of any of the above adjuvants is readily ascertained by one skilled in the art.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., decreasing or increasing Ire1 activity, and/or reducing, eliminating, or slowing the progression of disease symptoms. Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g., Alzheimer's disease), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. In one embodiment, the dosage range is 0.001% to 10% w/v. In another embodiment, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration and dosage can be chosen by the individual physician in view of the patient's condition and the particular method in which the compound is used.

I. EXAMPLES

The following examples are meant to illustrate certain embodiments of the invention and not to limit the scope of the invention described herein.

General Methods.

Proteins were expressed in *E. coli* and purified using GST-affinity purification and size exclusion chromatography. The DNA oligonucleotides were made by PCR and purchased from IDT. RNA oligonucleotides were purchased from Dharmacon Inc. or prepared by in vitro transcription with T7 RNA polymerase. All kinetic assays and analytical ultracentrifugation were done at 30° C. and neutral pH. Diffraction data were collected from cryo-preserved crystals at a beamline 8.3.1 (Advanced Light Source, Berkeley National Laboratories). Phases were determined by molecular replacement using PDB coordinates 2rio as a search model in PHASER. The final model contains amino acids 665-864, 892-1115 of Ire1; a part of the N-tail (641-664) and the hyperphosphorylated loop 865-891 (aF-aEF) are disordered. The final resolution is 3.9 Å, R/Rfree are 0.264/0.298 with excellent geometry. A detailed description of the experimental procedures is provided in below.

Example 1

Generic Chemical Syntheses

Certain compounds of the present invention may be synthesized using the Schemes below, making appropriate reagent selections as necessary.

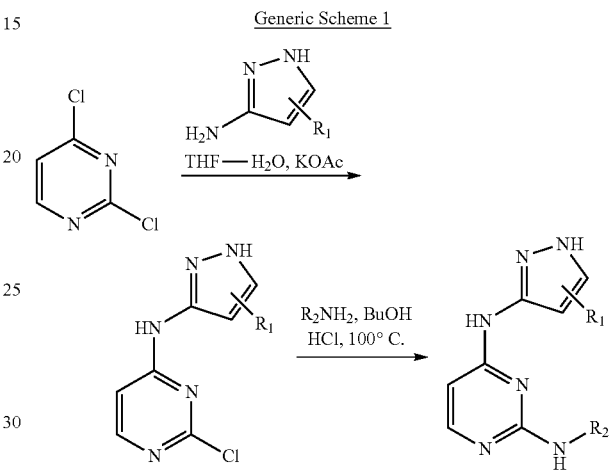

Generic Scheme 1

The variables $R_1$ and $R_2$ in Scheme 1 above are as defined for the variables $R^1$ and $R^2$, respectively, in the description of the Ire1 modulators described above. The above scheme may be modified according to known chemical synthesis techniques to obtain various embodiments of the chemical genuses set forth herein.

Example 2

Synthesis of APY24 using Generic Scheme 1

Step 1: Synthesis of the 4-pyrimidino-aminopyrazole intermediate. 2,4-dichloropyrimidine (3.2 g, 21.6 mmol) and 5-cyclopropyl-2H-pyrazol-3-ylamine (2.65 g, 21.5 mmol) were dissolved in a 1:1 mixture of THF and $H_2O$ (140 mL), treated with KOAc (30 eq., 64 g), and kept at 55° C. for 48 h. The layers were separated, and the organic layer was evaporated, dissolved in CH$_2$Cl$_2$ (30 mL), and kept at −20° C. for 3 h. Precipitated pyrimidino-aminopyrazole chloride salt was collected by filtration. Filtrates were evaporated, dissolved in CH$_2$Cl$_2$ (25 mL), kept at −20° C. for another 3 h, and filtered. Combined solids were dissolved in CHCl$_3$:CH$_3$OH 10:1 (25 mL) and purified (CHCl$_3$:CH$_3$OH=100:0→90:10), affording the pyrimidino-aminopyrazole intermediate (46% yield, 2.32 g). $^1$H NMR (400 MHz, DMSO) δ 12.14 (s, 1H), 10.23 (s, 1H), 8.10 (s, 1H), 1.84 (m, 1H), 0.88 (m, 2H), 0.64 (m, 2H). $^{13}$C NMR (100 MHz, DMSO) δ 161.4, 160.7, 160.0, 153.9, 148.6, 147.8, 146.8, 8.4, 8.2. MS calculated for C$_{10}$H$_{10}$ClN$_5$ 235.06 (M$^+$). found 236.15 (M$^+$).

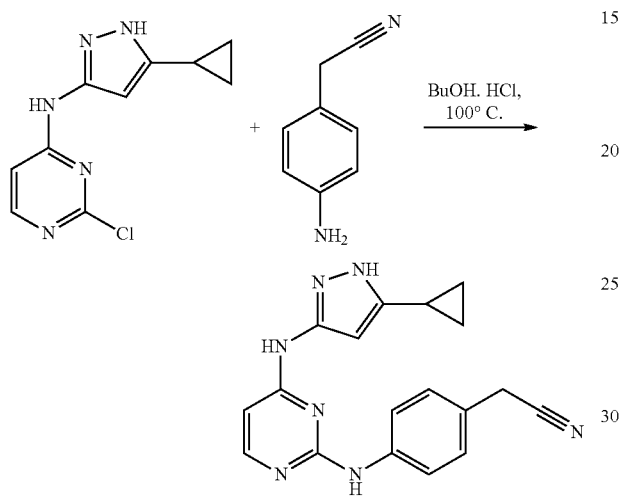

Step 2: Synthesis of APY24. The pyrimidino-aminopyrazole monochloride (0.2 g, 0.85 mmol) and p-aminobenzonitrile (0.112 g, 0.85 mmol) were dissolved in BuOH (8 mL) followed by the addition of concentrated HCl (0.1 mL). Resulting reaction mixture was kept at 100° C. overnight. Solid precipitates were collected by filtration, washed with BuOH (8 mL), and dried under vacuum affording compound APY24 (0.23 g, 86% yield). $^1$H NMR (400 MHz, DMSO) δ 11.46 (s, 1H), 10.98 (s, 1H), 7.96 (m, 1H), 7.48 (bs, 2H), 7.37 (d, 2H, J=8 Hz), 6.49 (bs, 1H), 6.01 (bs, 1H), 4.03 (s, 2H), 1.82 (m, 1H), 0.89 (m, 2H), 0.52 (bs, 2H). $^{13}$C NMR (100 MHz, DMSO) δ 160.3, 153.2, 147.6, 145.8, 143.2, 136.5, 129.4, 124.4, 119.8, 100.1, 94.1, 22.6, 8.8, 7.4. MS calculated for C$_{18}$H$_{17}$N$_7$ 331.15 (M$^+$). Found 332.11. (M$^+$).

Example 3

Synthesis of AD74

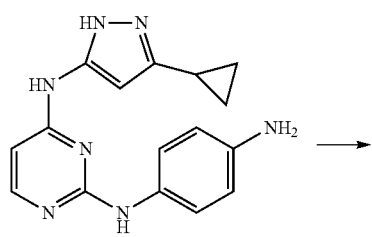

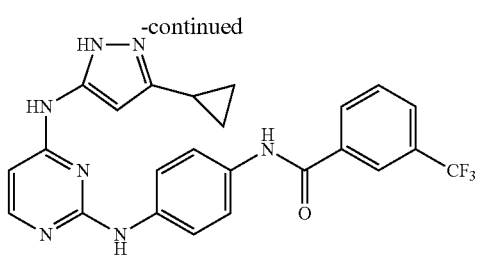

Synthesis of AD74: N-(4-(4-(3-cyclopropyl-1H-pyrazol-5-ylamino)pyrimidin-2-ylamino)phenyl)-3-(trifluoromethyl)benzamide. A solution of N2-(4-aminophenyl)-N4-(3-cyclopropyl-1H-pyrazol-5-yl)pyrimidine-2,4-diamine (0.011 g, 0.035 mmol; Shokat Lab: A. Statsyuk) in CH$_2$Cl$_2$ (10 mL) was cooled in an ice-water bath. To this 3-(trifluoromethyl)benzoyl chloride (0.005 mL, 0.036 mmol) diluted in CH$_2$Cl$_2$ (5 mL) was added drop wise. The reaction was allowed to warm and was left stirring for 1 hour. The reaction proceeded until completion as judged by TLC and LC-MS. The reaction mixture was concentrated in vacuo, resuspended in 50:50 H$_2$O—CH$_3$CN, and purified on a C18 column in CH$_3$CN/H$_2$O/0.1% TFA (1-100% gradient) to afford AD74. ESI-MS m/z[M+H]+. Found 480.5. Calculated 480.2.

Example 4

Synthesis of AD75

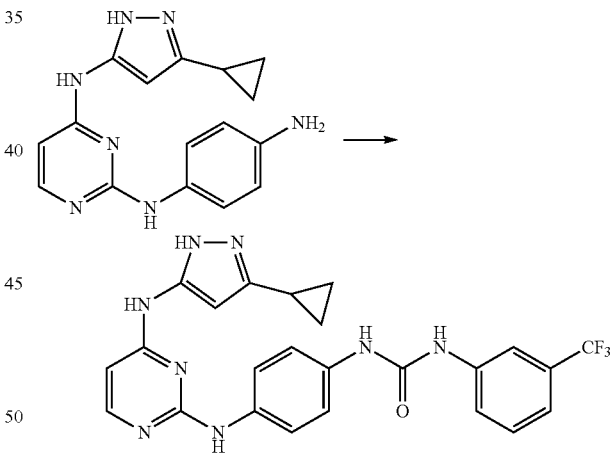

Synthesis of AD75: 1-(4-(4-(3-cyclopropyl-1H-pyrazol-5-ylamino)pyrimidin-2-ylamino)phenyl)-3-(3-(trifluoromethyl)phenyl)urea. A solution of N2-(4-aminophenyl)-N4-(3-cyclopropyl-1H-pyrazol-5-yl)pyrimidine-2,4-diamine (0.022 g, 0.07 mmol) in CH$_2$Cl$_2$ (10 mL) was cooled in an ice-water bath. To this 3-(trifluoromethyl)phenyl isocyanate (0.030 mL, 0.2 mmol) diluted in CH$_2$Cl$_2$ (5 mL) was added drop wise. The reaction was allowed to warm to room temperature and left stirring for 1 hour. The reaction proceeded until completion as judged by TLC and LC-MS. The reaction mixture was concentrated in vacuo, resuspended in 50:50 H$_2$O—CH$_3$CN, and purified on a C18 column in CH$_3$CN/H$_2$O/0.1% TFA (1-100% gradient) to afford AD75. ESI-MS m/z[M+H]+. Found 495.5. Calculated 495.2.

Example 5

Synthesis of AD76

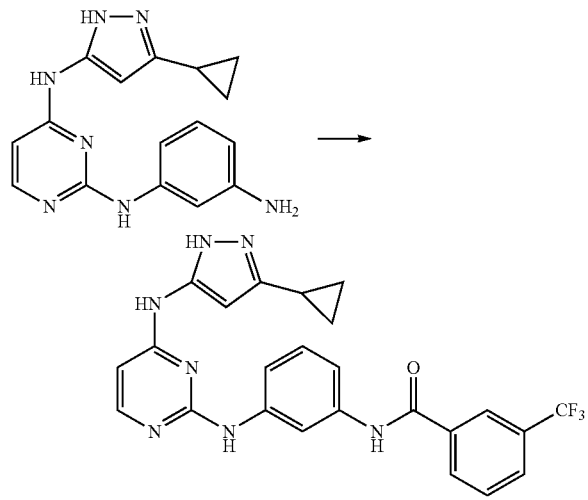

Synthesis of AD76: N-(3-(4-(3-cyclopropyl-1H-pyrazol-5-ylamino)pyrimidin-2-ylamino)phenyl)-3-(trifluoromethyl)benzamide. A solution of N2-(3-aminophenyl)-N4-(3-cyclopropyl-1H-pyrazol-5-yl)pyrimidine-2,4-diamine (0.014 g, 0.046 mmol; Shokat Lab: A. Statsyuk) in $CH_2Cl_2$ (10 mL) was cooled in an ice-water bath. To this 3-(trifluoromethyl)benzoyl chloride (0.007 mL, 0.046 mmol) diluted in $CH_2Cl_2$ (5 mL) was added drop wise. The reaction was allowed to warm and was left stirring for 1 hour. The reaction proceeded until completion as judged by TLC and LC-MS. The reaction mixture was concentrated in vacuo, resuspended in 50:50 $H_2O$—$CH_3CN$, and purified on a C18 column in $CH_3CN/H_2O/0.1\%$ TFA (1-100% gradient) to afford AD76. ESI-MS m/z[M+H]+. Found 480.4. Calculated 480.2.

Example 6

Synthesis of AD77

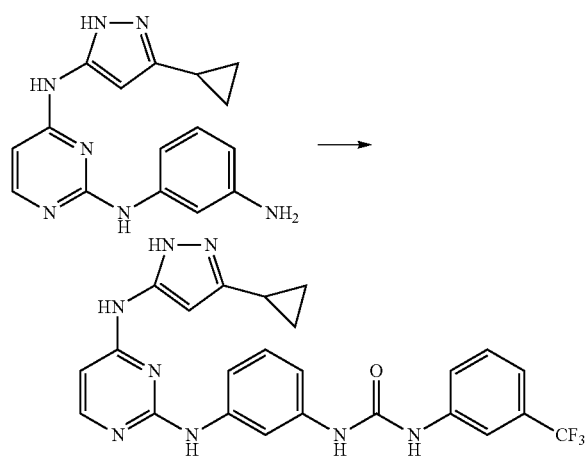

Synthesis of AD77: 1-(3-(4-(3-cyclopropyl-1H-pyrazol-5-ylamino)pyrimidin-2-ylamino)phenyl)-3-(3-(trifluoromethyl)phenyl)urea. A solution of N2-(3-aminophenyl)-N4-(3-cyclopropyl-1H-pyrazol-5-yl)pyrimidine-2,4-diamine (0.014 g, 0.046 mmol) in $CH_2Cl_2$ (10 mL) was cooled in an ice-water bath. To this 3-(trifluoromethyl)phenyl isocyanate (0.006 mL, 0.046 mmol) diluted in $CH_2Cl_2$ (5 mL) was added drop wise. The reaction was allowed to warm to room temperature and left stirring for 12 hours. The reaction proceeded until completion as judged by TLC and LC-MS. The reaction mixture was concentrated in vacuo, resuspended in 50:50 $H_2O$—$CH_3CN$, and purified on a C18 column in $CH_3CN/H_2O/0.1\%$ TFA (1-100% gradient) to afford AD77. ESI-MS m/z[M+H]+. Found 495.4. Calculated 495.2.

Example 7

Assay Methods

Expression and Purification of Ire1 Constructs.

The plasmids for Ire1 expression were prepared using PCR with Pfu polymerase and pGEX-6P-2 vector encoding the cytoplasmic domain of Ire1 (Sidrauski, C. et al., Cell 90:1031-9 (1997)). DNA primers for mutagenesis were designed using Biochem Lab Solutions 3.5 and purchased from IDT. Proteins were expressed in BL21 CodonPlus (RIPL) E. coli cells (Stratagene). Expression and purification was conducted as described previously (Nock, S. et al., Methods Enzymol 342:3-10 (2001)). We note that bacteria were grown at 22° C., and lysis and FPLC buffers contained at least 300 mM NaCl to prevent aggregation of Ire1. Protein concentrations were determined from UV spectra using absorption peak at 280 nm and calculated extinction coefficients (Biochem Lab Solutions 3.5). Purified Ire1 variants had concentrations 10-70 mg/ml and were greater than 99% pure as judged by Coomassie blue staining and quantitation of FPLC traces.

Preparation of RNA Substrates.

HP21 21-mer and HAC1 28-mer were purchased from Dharmacon Inc. Other RNA substrates were prepared from restriction-digested plasmids encoding for HAC1 and XBP1 mRNA or from PCR-amplified products. Preparative amounts of long RNA were prepared using MegashortScript kit (Ambion). Prior to use, the oligonucleotides were purified by a denaturing (8 M urea) 5-20% polyacrylamide gel electrophoresis (PAGE), cross-linked 29:1 (National diagnostics), eluted in TE buffer, and ethanol precipitated. The $^{32}$p-labeled at the 5'-terminus substrates were prepared using T4 PNK (NEB) and g-$^{32}$pATP by NEN. The $^{32}$p-body-labeled substrates were prepared by transcription with T7 RNA polymerase (Promega) in the presence of a-$^{32}$pUTP (NEN). The $^{32}$p-labeled substrates were purified by denaturing 5-20% PAGE, eluted in TE, and ethanol precipitated.

The RNase Cleavage Assay.

RNA cleavage reactions were conducted at 30° C. in buffer containing 20 mM HEPES (pH 7.5), 70 mM NaCl, 2 mM ADP (pH 7.0), 2 mM Mg(OAc)$_2$, 5 mM DTT, 5% glycerol, less than 1 nM $^{32}$p-labeled RNA substrate, and 3 nM-20 μM Ire1. Reaction solutions and buffers were designed using Biochem Lab Solutions 3.5. Reactions were prepared such that 1 μl of RNA was added to 9 μl of pre-warmed reaction mixture containing all components except RNA. Typically, 3-10 minute time courses were collected starting from 5 seconds for the first time point. At time intervals, 1 μl of solution was withdrawn from each reaction and mixed with 6 μl stop solution containing 10 M urea, 0.1% SDS, 0.1 mM EDTA, 0.05% xylene cyanol, and 0.05% bromophenol blue. The samples were separated by a denaturing 10% PAGE and exposed on a phosphor storage screen. The screens were scanned on a Storm or a Typhoon instrument and quantified using ImageQuant 5.0 or GelQuant.NET 1.4 programs. The data were plotted and fit in SigmaPlot 6.0.

Figure 20:
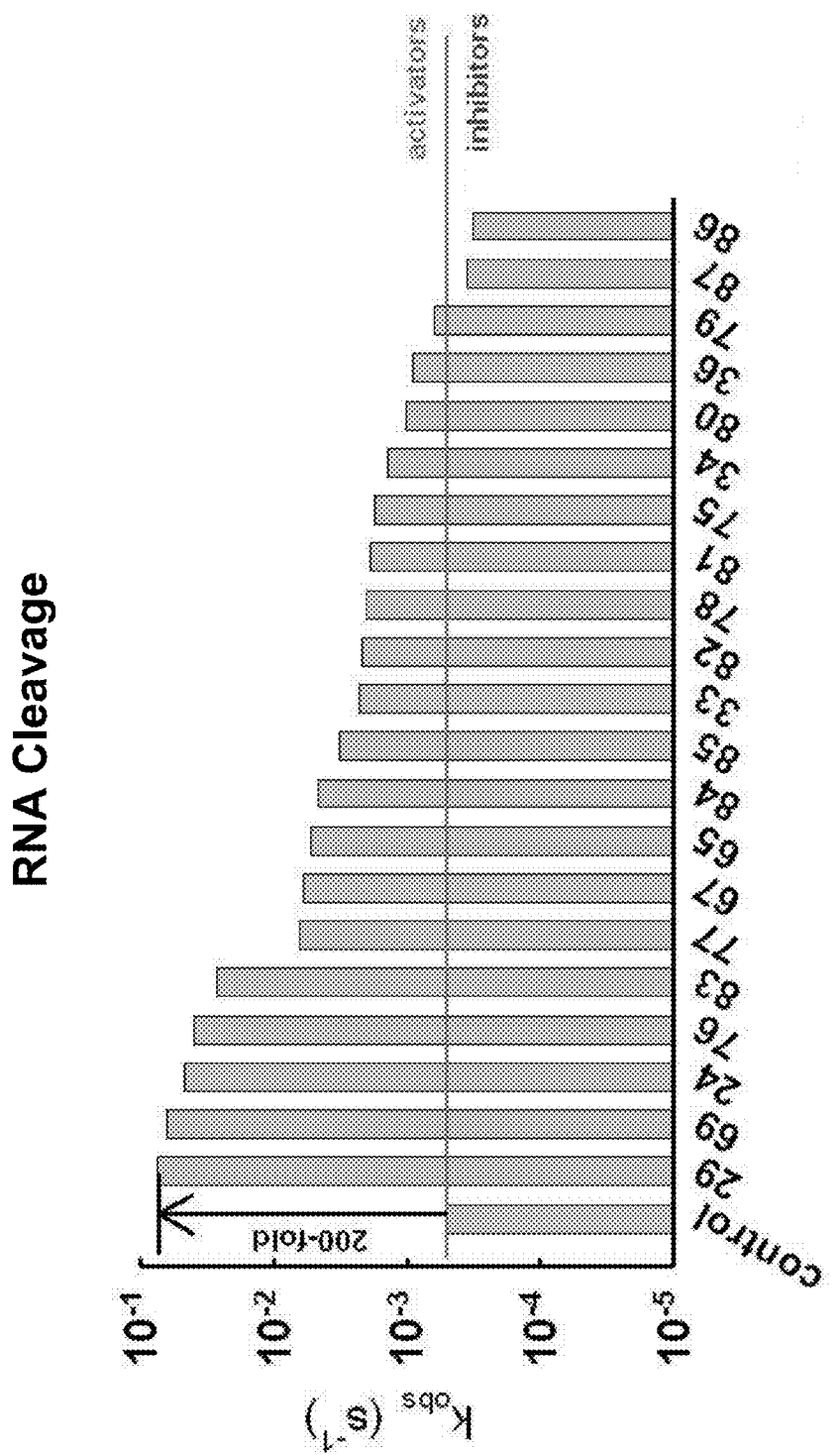
FIG. 20. RNA cleavage-based yIre1 activation assay with exemplary compounds.

RNA cleavage can be used to assess yIre1 activation as shown by FIG. 20 and the table below (3 μM yIre1, stem loop RNA, 15 μM effector):

| | |
|---|---|
| Control | 0.000504 |
| APY29 | 0.07509 |
| APY69 | 0.06355 |
| APY24 | 0.04667 |
| APY76 | 0.03994 |
| APY83 | 0.02693 |
| APY77 | 0.006479 |
| APY67 | 0.006034 |
| APY65 | 0.005304 |
| APY84 | 0.004672 |
| APY85 | 0.003287 |
| APY33 | 0.00232 |
| APY82 | 0.002172 |
| APY78 | 0.002028 |
| APY81 | 0.001872 |
| APY75 | 0.00175 |
| APY34 | 0.0014 |
| APY80 | 0.001022 |
| APY36 | 0.000897 |
| APY79 | 0.000626 |
| APY87 | 0.000358 |
| APY86 | 0.000324 |

Figure 21A:
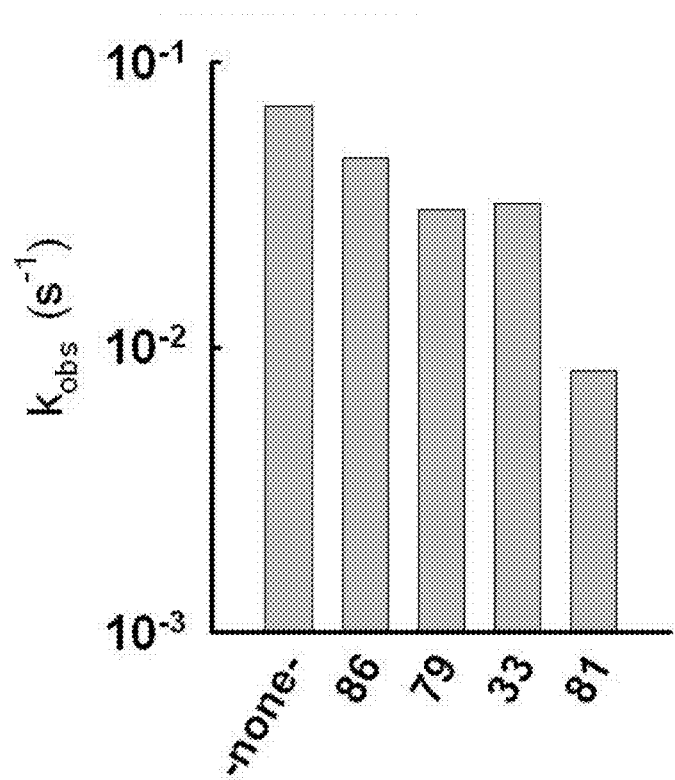
FIGS. 21A and B. A. RNA cleavage-based yIre1 inhibition assay with purified Ire1 under conditions that have pre-activated Ire1. Here, several compounds, most notably, APY81, inhibit Ire1. Thus, some APY compounds could serve as both Ire1 RNase inhibitors or Ire1 RNase activators, depending on the experimental setting.
Figure 21B:
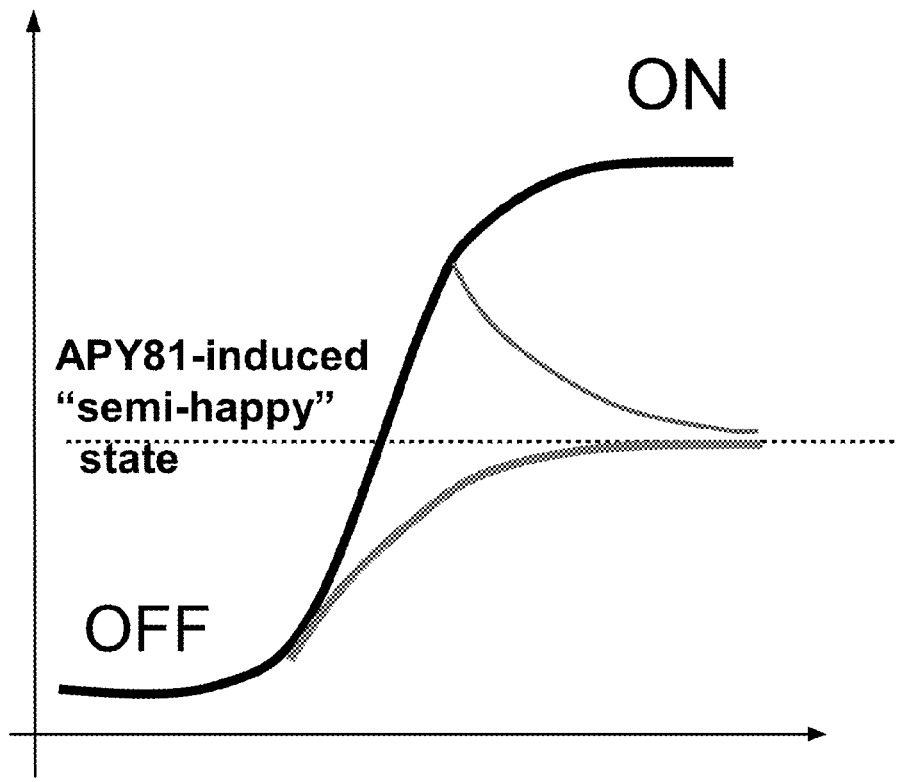
Figure 22:
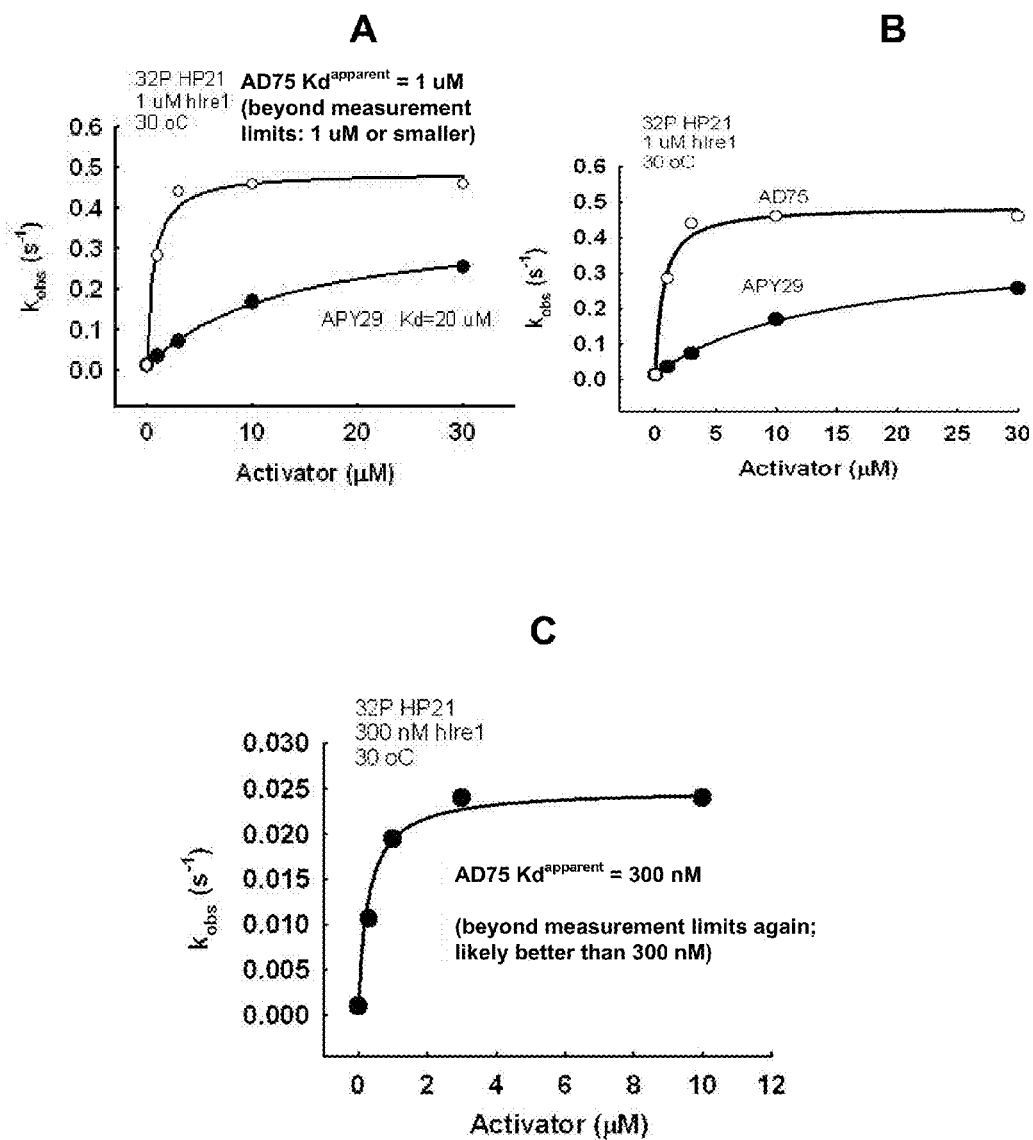
FIG. 22. Titrations of APY29 and AD75 with hIre1.

An RNA cleavage inhibition assay was also performed with exemplary compounds as shown by FIG. 21A (1.5 μM yIre1, stem loop RNA, 100 μM ADP-2 mM Mg, 30 μM effector).

Analytical Ultracentrifugation.

Ire1 samples (10 μM) were loaded to a 400 μl cell in buffer used for the RNase cleavage assay. Centrifugation was carried out on a Beckmann XL-A analytical ultracentrifuge at 55,000 rpm and at 30° C. A total of 60 scans were collected with a frequency of 1 scan per two minutes. Sedimentation traces were analyzed in UltraScan 6.0 using C(s) distribution with an average axial ratio 3:2.

Mass Spectrometry.

A gold-coated plate was washed with 100% methanol and water. Solution A (10 mg 4-HCCA in 0.7 ml of acetonitrile, 0.1% trifluoroacetic acid) was quickly spread in a layer and allowed to dry. The residue was removed gently with a tissue. Next, 0.5 μl of a mixture containing 1 μl Ire1 sample (0.1-1 mg/ml) and 5 μl solution B (300 μl formic acid, 100 μl $H_2O$, 200 μl iso-propanol, and 10 mg 4-HCCA) was spotted over the dried surface and allowed to dry. The sample was washed twice with 2 μl of 0.1% trifluoroacetic acid and used for MALDI analysis on a Voyager mass spectrometer. The spectra were analyzed using MoverZ.

Crystallization.

Initially, Ire1KR32 (10 mg/ml) was crystallized by vapor diffusion as a complex with ADP (2 mM) from 1.0 M sodium citrate. These co-crystals were disordered in one direction preventing their use in diffraction studies. A different crystal form was obtained by replacing the ADP with a kinase inhibitor APY29. Ire1KR32.APY29 crystals were obtained by vapor diffusion in hanging drops. Drops were prepared by mixing 1 μl of Ire1KR32 (12 mg/ml) and APY29 (1.2 mM) in storage buffer (20 mM HEPES pH 7.0 (20° C.), 300 mM NaCl, 2 mM DTT, and 5% glycerol) with 1 μl of solution containing 0.27 M $Na_2SO_4$, 8% PEG-3350, 10 mM EDTA, and 2 mM TCEP. Well solution contained 200 μl of 0.085 M $Na_2SO_4$, 2.33% 3350, and 5% tert-Amyl alcohol. Single crystals grew at room temperature to a maximum size of 0.1×0.4× 0.2 mm during three to four days. We found that TCEP could be replaced with 10 mM L-cysteine. For cryo-protection, the crystals were flash-frozen in solution containing 0.085 M $Na_2SO_4$, 3% tAm, 5% PEG-3350, and 30% ethylene glycol.

Data Collection and Analysis.

X-ray diffraction data were recorded on a beam line BL 8.3.1 at the Advanced Light Source at Berkeley National Laboratory. The data set, obtained using an X-ray wavelength of 1.11587 Å and an oscillation angle of 1 degree, was indexed, integrated, and scaled using the XDS package (Kabsch, W. *J Appl Cryst* 26:795-800 (1993)) (FIG. 14). 5% of the reflections were marked as test-set ($R^{free}$ set) reflections to monitor the progress of refinement. A molecular replacement solution was found by using PHASER (McCoy, A. J. *J Appl Cryst* 40:658-674 (2007)). 14 copies of monomer A from a recent X-ray structure of the Ire1 dimer (Lee, K. P. et al., *Cell* 132:89-100 (2008)) were used as a starting model for refinement. Simulated annealing and grouped B-factor refinement in CNS (Brunger, A. T. et al. *Acta Crystallogr D Biol Crystallogr* 54:905-21 (1998)) and, at final stages, PHENIX (Adams, P. D. et al., *Acta Crystallogr D Biol Crystallogr* 58:1948-54 (2002)) was carried out using 14-fold NCS. Fourier $s_A$-weighted (Read, R. J. *Acta Cryst A* 42:140-149 (1986)) $F_{obs}-F_{calc}$ difference maps were used for interpretation of the parts of the model missing from the starting structure. The model of the ligand was created using ChemSketch 10.0 (ACD labs). Model building and local real-space refinement were performed in Coot (Emsley, P. et al., *Acta Crystallogr D Biol Crystallogr* 60:2126-32 (2004)), Pymol (W. DeLano) and RSRef (Korostelev, A. et al., *Acta Crystallogr D Biol Crystallogr* 58:761-7 (2002)). The resulting model has excellent stereochemical parameters (FIG. 14) and low crystallographic $R/R^{free}$ of 0.264/0.298 indicating good agreement with diffraction data.

Cellular Assay.

Figure 17:
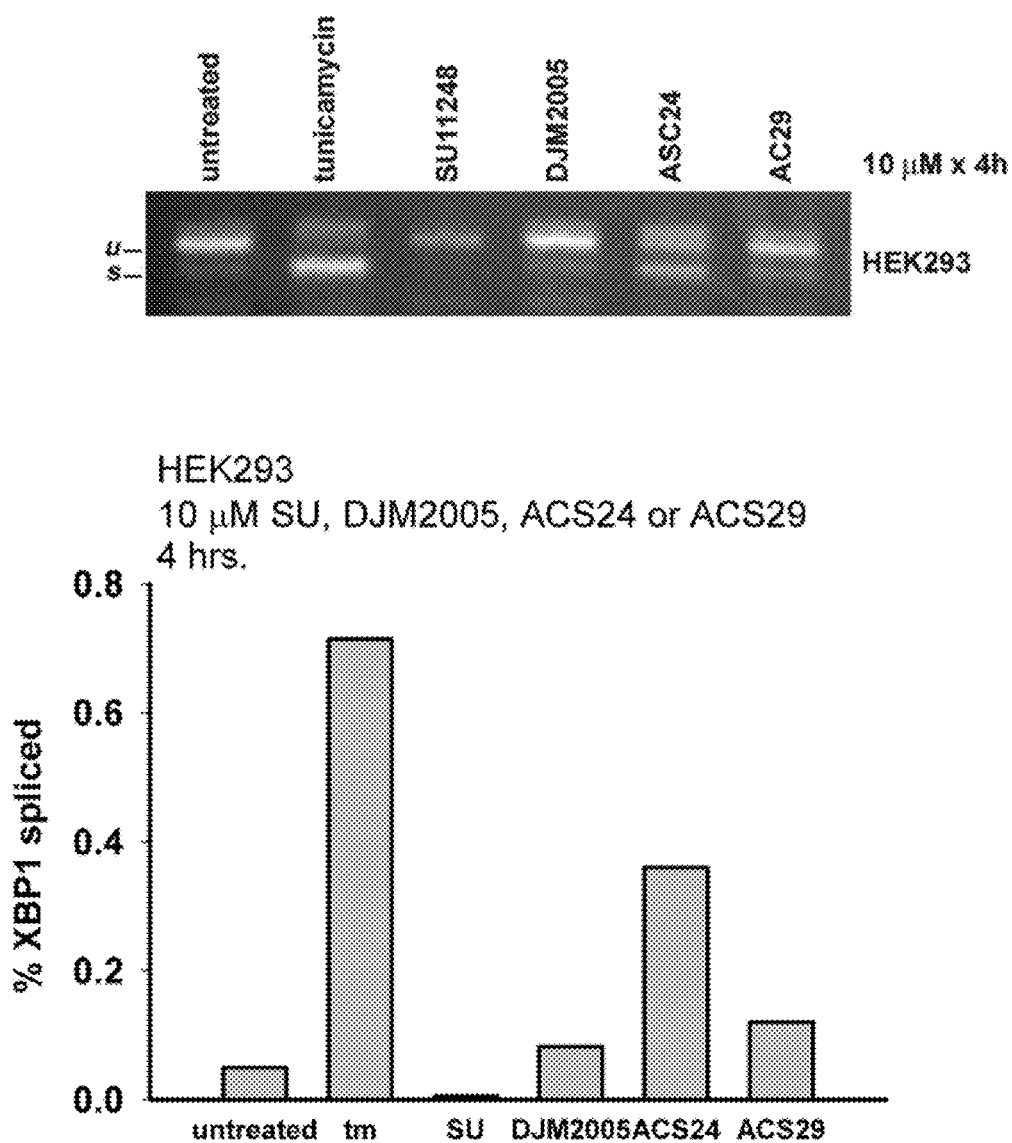
FIG. 17. Ire1 activation by APY29 and APY24 in HEK 293 cells.

The effect of tunicamycin, SU11248, DJM2005, APY24, and APY29 on Ire1 activity was tested in mammalian cells using HEK293 cells as a model system. Cells were treated according to the methods described in Lin J H et al., Science 318:944 (2007). After treatment with the corresponding agents for the indicated time, Xbp-1 mRNA splicing was determined by RT-PCR. Unspliced (u) and spliced (s) Xbp-1 mRNA products are indicated and serve as a measure of UPR activation through Ire1. Results are set forth in FIG. 17.

Figure 18:
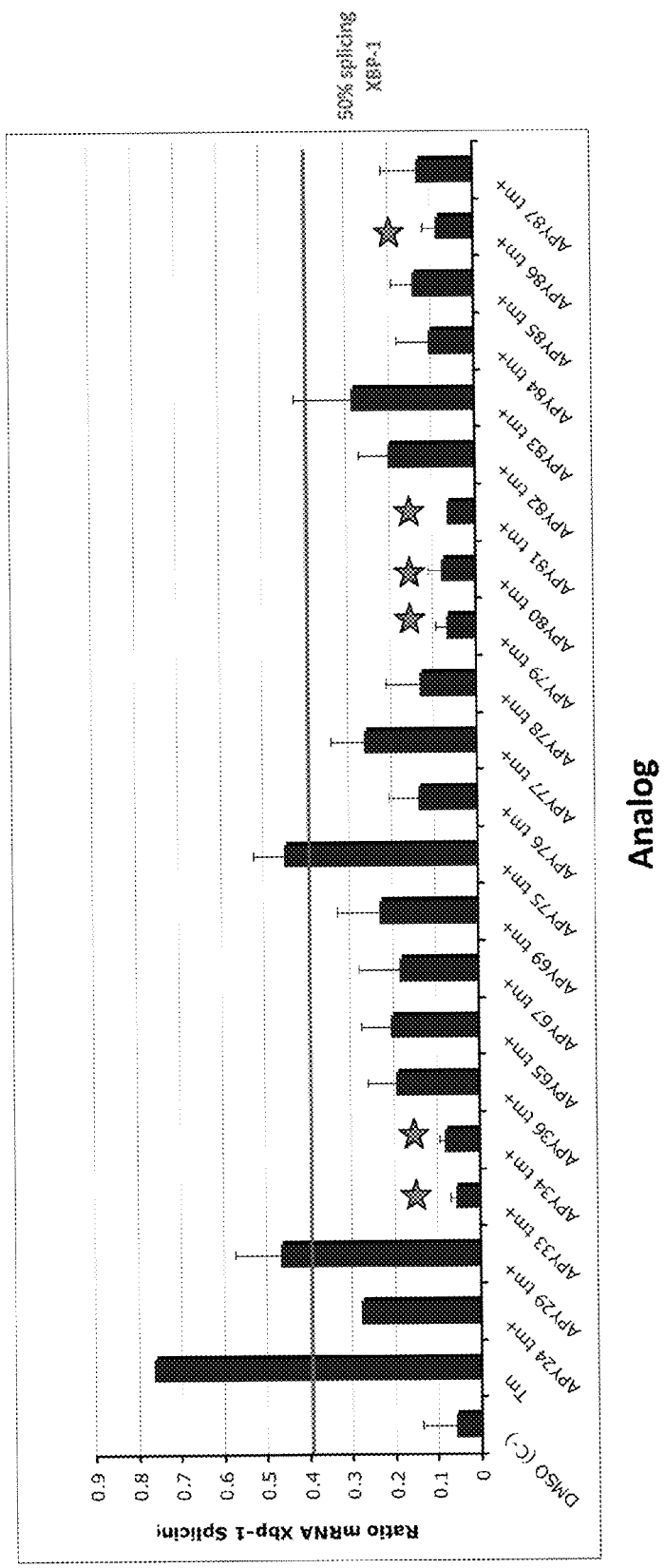
FIG. 18. UPR inhibition with exemplary compounds.
Figure 19:
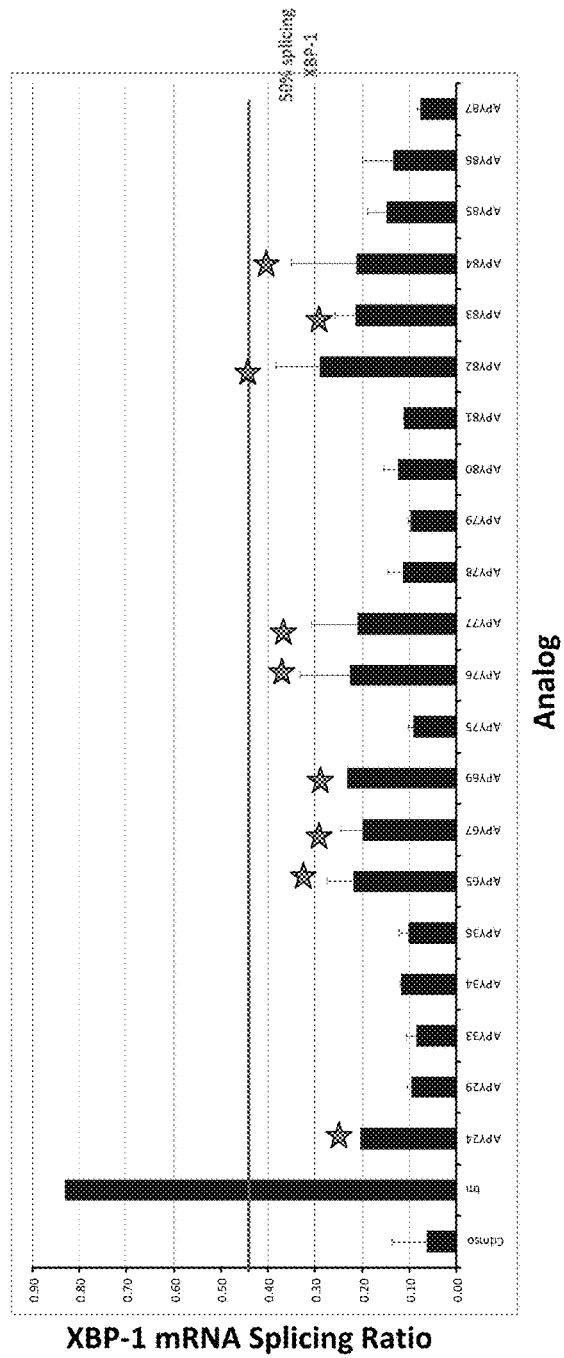
FIG. 19. UPR activation with exemplary compounds.

Exemplary compounds were assayed for their effect on UPR. Results are set forth in FIGS. 18-19 and in the table below.

| | % splicing mRNA XBP-1.Average | | |
|---|---|---|---|
| C DMSO | | 6% | |
| Tm | | 78% | |
| Compound | Tm 0.3 ug/ml + compound 2 μM | compound 2 μM | compound 10 μM |
| APY24 | 28% | 30% | 44% |
| APY29 | 40% | 10% | 14% |
| APY33 | 8% | 8% | 18% |
| APY34 | 7% | 12% | 34% |
| APY36 | 16% | 10% | 19% |
| APY65 | 29% | 22% | 51% |
| APY67 | 21% | 20% | 66% |
| APY69 | 36% | 23% | 40% |
| APY75 | 44% | 9% | 17% |
| APY76 | 11% | 23% | 39% |
| APY77 | 37% | 21% | 37% |
| APY78 | 11% | 11% | 27% |
| APY79 | 6% | 10% | 27% |
| APY80 | 9% | 12% | 28% |
| APY81 | 7% | 11% | 16% |
| APY82 | 27% | 29% | 27% |
| APY83 | 29% | 21% | 55% |
| APY84 | 12% | 21% | 60% |

-continued

| | | | |
|---|---|---|---|
| APY85 | 13% | 15% | 14% |
| APY86 | 9% | 13% | 42% |
| APY87 | 14% | 8% | 27% |

RT-PCR on Hek293 cells treated for 4 hrs

In vitro cleavage of $^{32}$P-stem-loop RNA by human Ire1, with AD series of Ire1 modulators gave the following results:

| | |
|---|---|
| Blank | 8.8310e-3 |
| AD74 | 0.0877 |
| AD75 | 0.2317 |
| AD76 | 0.0139 |
| AD77 | 0.0239 |

Assays for cross-reactivity with Src and Abl were also conducted. Purified c-Src or Abl were diluted in kinase reaction buffer (10 mM HEPES (pH 7.2), 10 mM MgCl$_2$, 0.2 mM DTT) to a concentration of approximately 10 nM and pre-incubated with 1 mg/mL BSA, 2.5% (v/v) DMSO, 133 μM peptide (sequence EAIYAAPFKKK for Abl and EIYGEFKKK for c-Src), and varying concentrations of inhibitor. Kinase reactions were initiated by the addition of 100 mM cold ATP supplemented with 5 mCi γ$^{32}$P ATP and allowed to proceed at room temperature (RT). At 10 minutes 1 mL of the reactions were spotted onto phosphocellulose sheets (P81, Whatman) and subsequently soaked in wash buffer (1.0% (v/v) phosphoric acid). The sheets were washed five times in buffer, dried, and transferred radioactivity was measured by phosphorimaging using a Typhoon™ scanner (Molecular Dynamics). Radioactive counts were quantified using ImageQuant software, and titration data were fit to a sigmoidal dose response to derive IC$_{50}$ values using the Prism® software package. Dose responses were based on a 12 point inhibitor titration, using 1/3 dilutions starting from 100 mM.

| Name | IC50 WT Src (nM) | IC50 WT Abl (nM) |
|---|---|---|
| AD74 | 356.5 | 2153.5 |
| AD75 | 170.3 | 2427.7 |
| AD76 | 138.1 | 4960.5 |
| AD77 | 442.1 | 36850.0 |

In Vitro Screening Methods.

To identify activators and inhibitors of Ire1, specific in vitro assays are performed.

1) Solution Transparency Assay:

For the identification of activators this assay uses any of the methods suitable for detecting protein aggregation in solution. In the most primitive form, a simple visual check of Ire1 solutions in neutral buffers containing ~300 mM NaCl and 5-100 mg/ml Ire1 is performed. Addition of an activator will cause cloudy appearance (FIG. 2A). This screen is rapid, is high-throughput and is suitable for easy automation. Alternatively, light scattering by a solution can be measured using dynamic light scattering (DLS) or static light scattering (SLS) approaches. Conditions for the screen are chosen such that adding of ADP or known activator (APY29) to the solution causes an appearance of heavy species as detected by n DLS or SLS approach. Successful activators will cause oligomer formation. Other methods of detecting protein aggregation known to a person of skill in the art will be equally valid.

Inhibitors are found by conducting the same screen in reverse, i.e. test compounds are added to Ire1 aggregates pre-formed in the presence of ADP or synthetic activator. The reverse changes (dissolution of aggregates) are being monitored. A successful inhibitor will be able to dissolve aggregates.

2) Fluorescence Resonance Energy Transfer (FRET) Assays:

The advantage of this assay is high sensitivity to activating molecules and ability to conduct measurements at very dilute Ire1 concentrations, where tightly binding activators and inhibitors are more easily selected from the sea of weaker-interacting activators and inhibitors. Ire1 used in the assay is a mixture of Ire1 labeled with a donor fluorophor (Ire1-FRET-D) and Ire1 labeled with an acceptor fluorophor (or a quencher dye) (Ire1-FRET-A|Q).

Fluorophors are covalently attached to Ire1 using cysteine chemistry or any other state of the art means of labeling proteins. The positions of the fluorophors are carefully chosen such as they are solvent exposed and are not located at any of the protein-protein interfaces; not blocking the active sites of kinase and RNase; and do not cause or block possible protein rearrangements, i.e. the labels should be neutral to the protein. Importantly, the labels should reside at such a distance that FRET between the labels is possible upon assembly of the composite oligomer from a mixture of Ire1-FRET-D and Ire1-FRET-A|Q. The screen for activating and inhibiting compounds is done as described above, except at much lower Ire1 concentrations that still produce a useful signal change upon adding test compounds such as ADP or APY29. Signal detection is done using fluorescence of a donor or/and an acceptor dye.

Exemplary compounds were assayed and the results are set forth in the table below.

| | Mean fluorescence | | % fold induction to Control | |
|---|---|---|---|---|
| C DMSO | 2427 | | 0% | |
| Tm | 3869 | | 59% | |
| Compound | Tm 0.3 ug/ml + compound 2 uM | compound 2 uM | Tm 0.3 ug/ml + compound 2 uM | compound 2 uM |
| APY24 | 2387 | 2569 | −2% | 6% |
| APY29 | 4016 | 2697 | 65% | 11% |
| APY33 | 3613 | 2811 | 49% | 16% |
| APY34 | 4318 | 2836 | 78% | 17% |
| APY67 | 2289 | 2326 | −6% | −4% |
| APY69 | 2805 | 2864 | 16% | 18% |
| APY77 | 2648 | 2570 | 9% | 6% |

FACS on Hek293-FT cells transfected with XBP1-GFP reporter treated for 24 hrs

3) Kinetic Assays:

Kinetic assays are described as in Lin J H et al., Science 318:944 (2007). Radio-labeled or fluorescently labeled RNA oligonucleotide that is cleaved by Ire1 is used as substrate. Screening RNA cleavage reactions are carried out at a Ire1 concentration that produces strongest activity response to test compounds (ADP and APY29). Activator and inhibitor screens are related as described above.

Results

Variants of the cytosolic portion of Ire1 that contain the kinase and the RNase domains (Ire1KR) and Ire1KR extended by 24 (Ire1KR24) or 32 (Ire1KR32) amino acids towards the N-terminus (FIG. 1A, FIG. 1C, FIG. 7) were prepared. These additional amino acid extensions are part of a ~100 amino acid-long linker domain that tethers the kinase/RNase domains to the transmembrane domain. All three constructs cleaved site-specifically 5'-32p-labeled stem-loop oligoribonucleotides 14 derived from the XBP1 mRNA (FIG. 1B, FIG. 8). The observed rate constant for cleavage of a 21-mer stem-loop HP21 exhibited a non-Michaelis dependence on the enzyme concentration and increased cooperatively with a Hill coefficient n=2 for Ire1KR and Ire1KR24 and, surprisingly, a Hill coefficient n=3.5-8 for Ire1KR32 (FIG. 1D). This observation suggests that the RNase activity of Ire1 arises from self-association with the formation of predominantly dimers for Ire1KR and Ire1KR24, and oligomers for Ire1KR32. No ADP.Mg co-factor was required for the cooperative activation of the RNase. However, co-factor increased the specific RNase activity on average by two orders of magnitude, indicating that it stimulates the activating transition (see Mechanistic implications).

At protein concentrations above 10 µM, reactions with Ire1KR32 appeared as a cloudy, heterogeneous suspension, indicating high-order oligomerization of Ire1KR32 (FIG. 1D, FIG. 2A). The presence of several oligomeric species of Ire1KR32 was apparent upon analytical ultracentrifugation of the sample (FIG. 2B). The oligomerization could be readily reversed and the RNase activity be suppressed by addition of salt to the solution (FIG. 2A, FIG. 2C). By contrast, solutions of Ire1KR and Ire1KR24 remained clear at all concentrations of the proteins and did not show physical signs of protein oligomerization, as expected from the lower cooperativity of their activation profiles in FIG. 1D.

Ire1KR32 exhibits a ~$10^2$-fold larger specific RNase activity than do Ire1KR and Ire1KR24 against HP21 (FIG. 2D, left panel). The observed rate constants are compared at 1 µM concentration of the enzymes, where reactions occur in the same kinetic regime characterized by a log-linear concentration response of the observed rate constant. The catalytic advantage of Ire1KR32 is even more apparent with a longer substrate, XBP1 443-mer, which more closely mimics Ire1's natural mRNA substrate (FIG. 2D, right panel). Under the conditions shown, Ire1KR32 cleaves this substrate ~$10^4$-$10^5$-fold faster than do Ire1KR24 and Ire1KR. These observations show that eight basic amino acids within the N-terminal linker domain that constitute the difference between Ire1KR32 and Ire1KR24 (FIG. 7) define the self-association properties and the specific RNase activity of the cytosolic domains of Ire1. The use of Ire1 domain that includes this extended N-terminus was important in obtaining the crystal structure of the oligomeric state of Ire1 (below).

Wild-Type Ire1 Activation.

Figure 3:
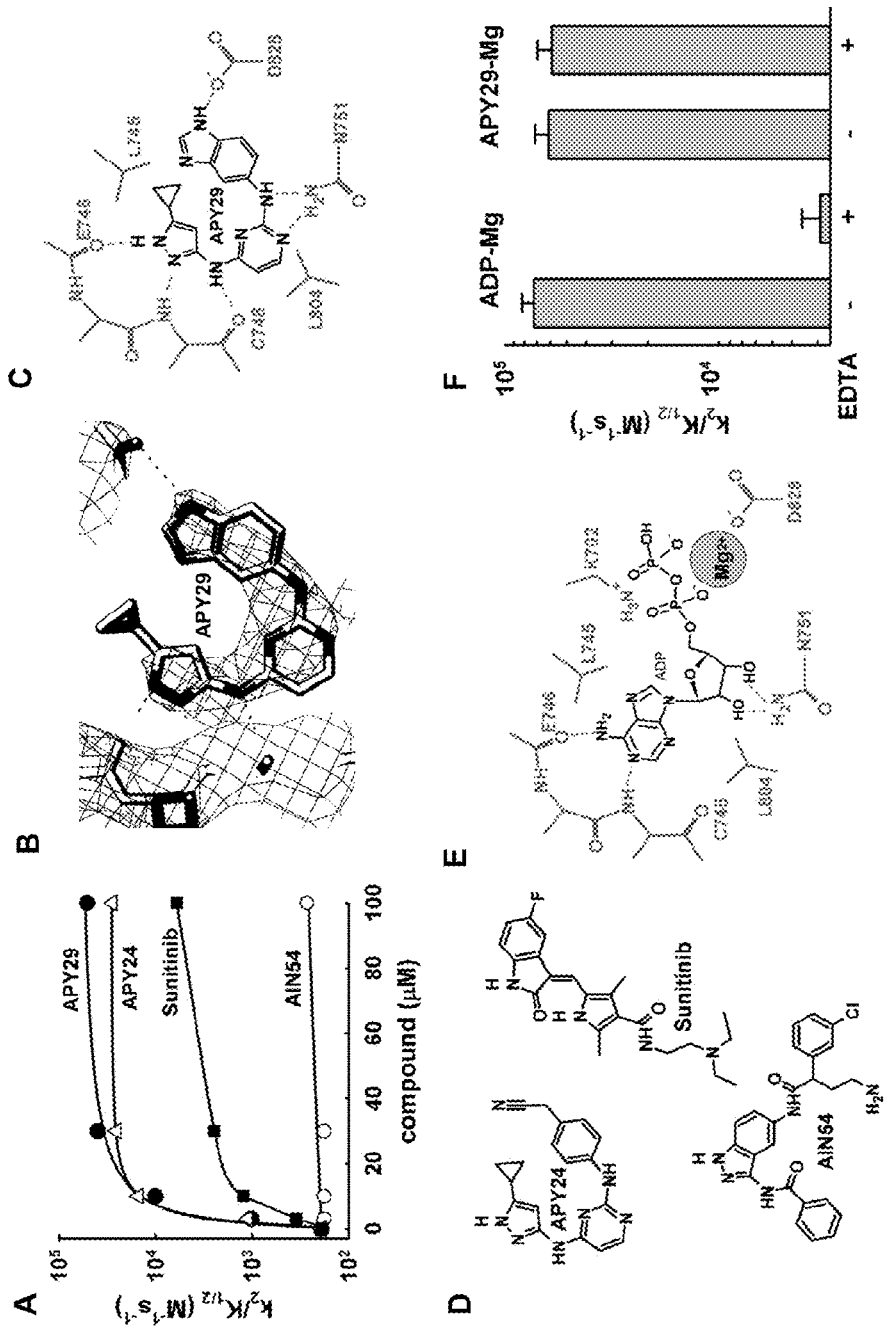
FIG. 3. Kinase inhibitors activate the RNase of wild type Ire1. A. Inhibitors of serine and tyrosine kinases activate the RNase of Ire1KR32. B. A well-resolved electron density for APY29 bound to the ATP pocket of the Ire1KR32 kinase. C. The network of interactions between APY29 and the ATP pocked of Ire1KR32 kinase. D. Structures of APY24, Sunitinib and AIN54 with proposed hydrogen bonds to Ire1 shown by dashed lines. E. The network of interactions between ADP-Mg and ATP pocket of Ire1 kinase in the Ire1 dimer structure. F. Chelation of magnesium from the reaction buffer inhibits RNase activity of Ire1KR32 in the presence of ADP, but not APY29.

Ire1KR32 was co-crystallized with inhibitors that were designed to target CDK2 and EGFR kinases. Certain kinase inhibitors fully activated the RNase function of Ire1 (FIG. 3A). This is the first example of wild-type Ire1 activation by synthetic compounds.

Crystals obtained with the inhibitor APY29 allowed the structure determination of the Ire1KR32-APY29 complex at 3.9 Å resolution. Data statistics are summarized in FIG. 15. A well-resolved density for the inhibitor molecule was found in the ATP binding pocket of the Ire1 kinase domain (FIG. 3B). APY29 forms an extensive hydrogen-bonding network with the protein backbone formed by E746, L747, and C748 (FIG. 3C). Hydrogen bonds are likely to also form with two side chains at the active site, N751, and D828. Comparison of the inhibitor structures shows that all tested compounds can form hydrogen bonds with the protein backbone (FIG. 3D). Potent activators such as APY29 and APY24 can in addition form hydrogen bonds with the side chain N751 and insert bulky aromatic rings in place of the sugar-phosphate moiety of ADP. Manual fitting of sunitinib guided by known structures of kinase inhibitor complexes (e.g., PDB IDs 2G9X and 2F4J) predicts that the compound fills the nucleobase site, but not the sugar and the phosphate sub-sites. Such partial occupancy is consistent with the fairly good binding of sunitinib to Ire1 accompanied by only a partial activation of the enzyme (FIG. 3A). AIN54 could not be readily fit to the ATP pocket due to steric clashes arising partly because of the unusual position of beta strand β1 that covers the nucleotide-binding pocket of the Ire1 kinase.

The interactions of APY29 with the nucleotide-binding pocket closely mimic those of the native co-factor, ADP (FIG. 3E), except the inhibitor does not use a divalent metal ion for docking. This structural difference provides an excellent tool to test the role of magnesium in the RNase activity of Ire1. Accordingly, the effect of EDTA on the RNase activity of Ire1KR32 was examined. For reactions stimulated by ADP, the RNase activity decreased by greater than an order of magnitude, whereas for reactions stimulated by APY29 the RNase activity remained unchanged (FIG. 3F). Thus, Ire1's RNase activity does not require divalent metal ions, demonstrating that magnesium only serves for ADP binding apparently by linking the negatively charged phosphate moiety of ADP with the carboxyl group of D828.

Together, these observations show that ADP and inhibitors activate Ire1 RNase by filling the ATP pocket. For maximum activity the nucleobase and the sugar position should be occupied to stabilize the active open conformation of the kinase that favors self-association of Ire1. Electrostatic interactions due to coordination of the metal ion and the phosphate groups of ADP do not play a specific role and can be replaced with neutral space-filling groups.

Figure 2:
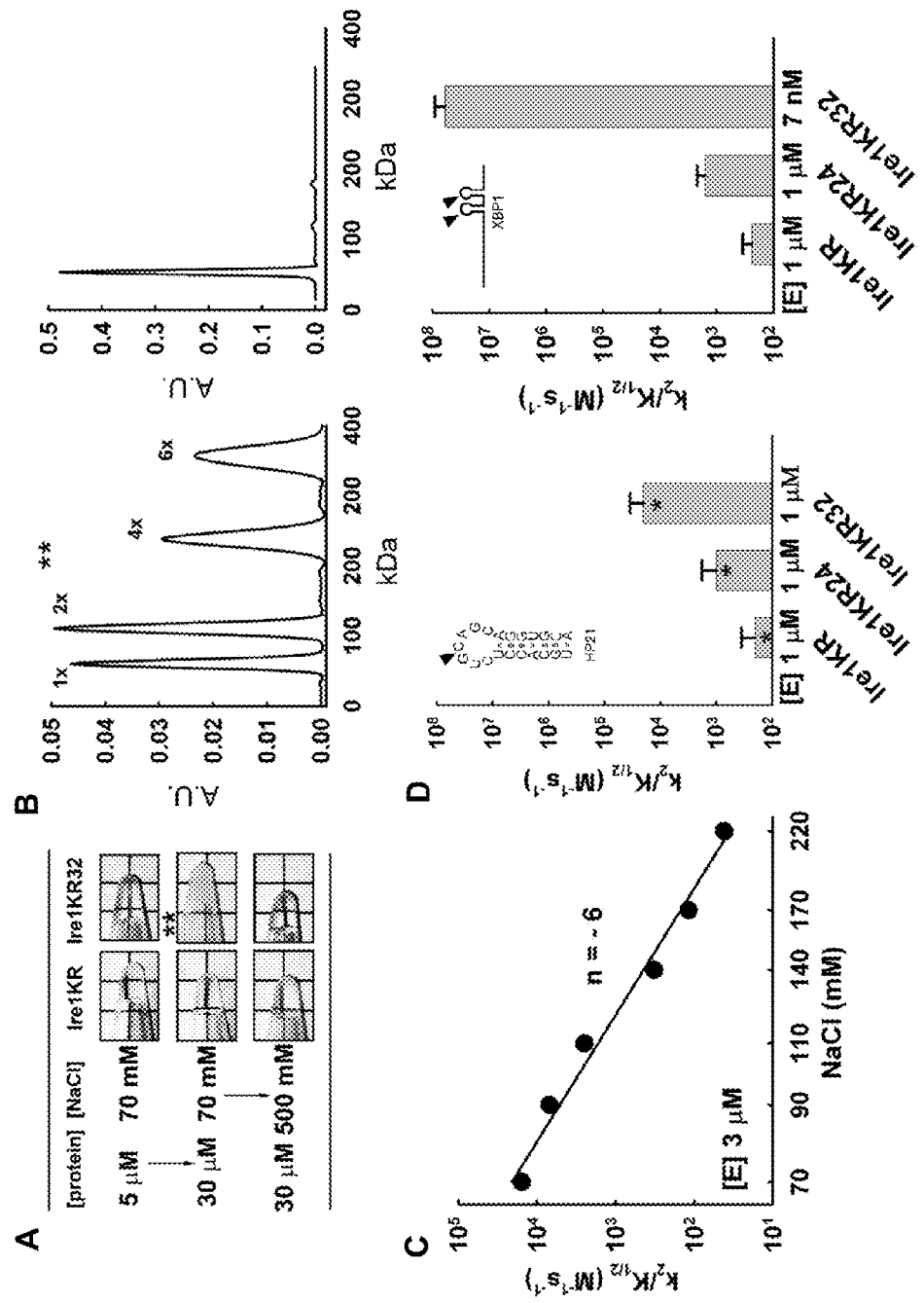
FIG. 2. Linker controls the oligomerization and activation of Ire1. A. Ire1KR is soluble at all concentrations tested, whereas Ire1KR32 forms cloudy solutions above 10 µM concentration. B. Analytical ultracentrifugation of Ire1KR32 under conditions of aggregation (a) reveals monomers, dimers and higher-order assemblies. C. Salt cooperatively inhibits the RNase activity of Ire1KR32. D. Ire1KR32 exhibits higher RNase activity during cleavage of HP21 and XBP1, compared to Ire1KR and Ire1KR24.
Figure 4:
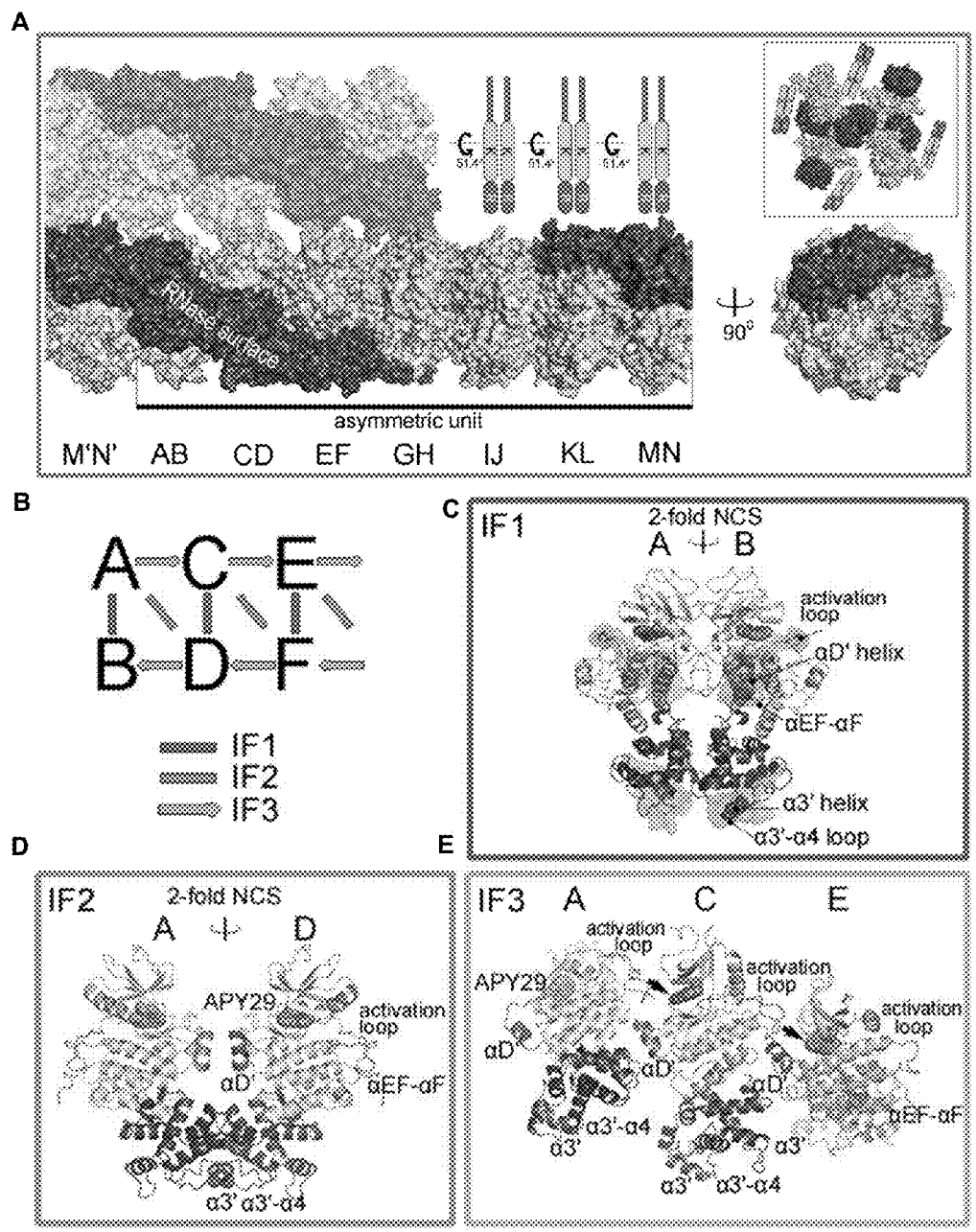
FIG. 4. Structure of the oligomer formed by the cytosolic domain of Ire1. A. Ire1KR32 assembles in extended tubular oligomers. B. Monomers pack in the oligomer in an anti-parallel double-strand arrangement. C. IF1 of Ire1KR32.APY29 is similar to that in the Ire1-ADP co-crystal structure. D. IF2 has a 2-fold non-crystallographic symmetry and involves diagonally located Ire1 monomers that form a new RNase-RNase interface (IF2) as well as a smaller kinase-RNase interface (IF2). E. IF3 forms between monomers of the same "strand" of the oligomer, involves only kinase-kinase interactions and positions the activation loop suitably for trans-autophosphorylation.

In contrast to the crystal structure of Ire1 that lacks the oligomerization-inducing N-terminal segment and crystallizes as a dimer (FIG. 1, FIG. 2, FIG. 7), Ire1KR32 crystallizes as a symmetric high-order assembly (FIG. 4A). Fourteen molecules of Ire1KR32 constitute the asymmetric unit in the crystal lattice. Formation of the oligomer can be described as an incremental addition of symmetric Ire1 dimers to a side of a growing filament, with a simultaneous clockwise turn of 51.4° per dimer, with a complete 360° turn every 14 molecules. Such stepwise oligomerization mechanism apparently takes place in the solution, as analytical ultracentrifugation of Ire1KR32 shows monomers, dimers, tetramers, and hexamers but lacks trimers and pentamers (FIG. 2B).

Figure 9:
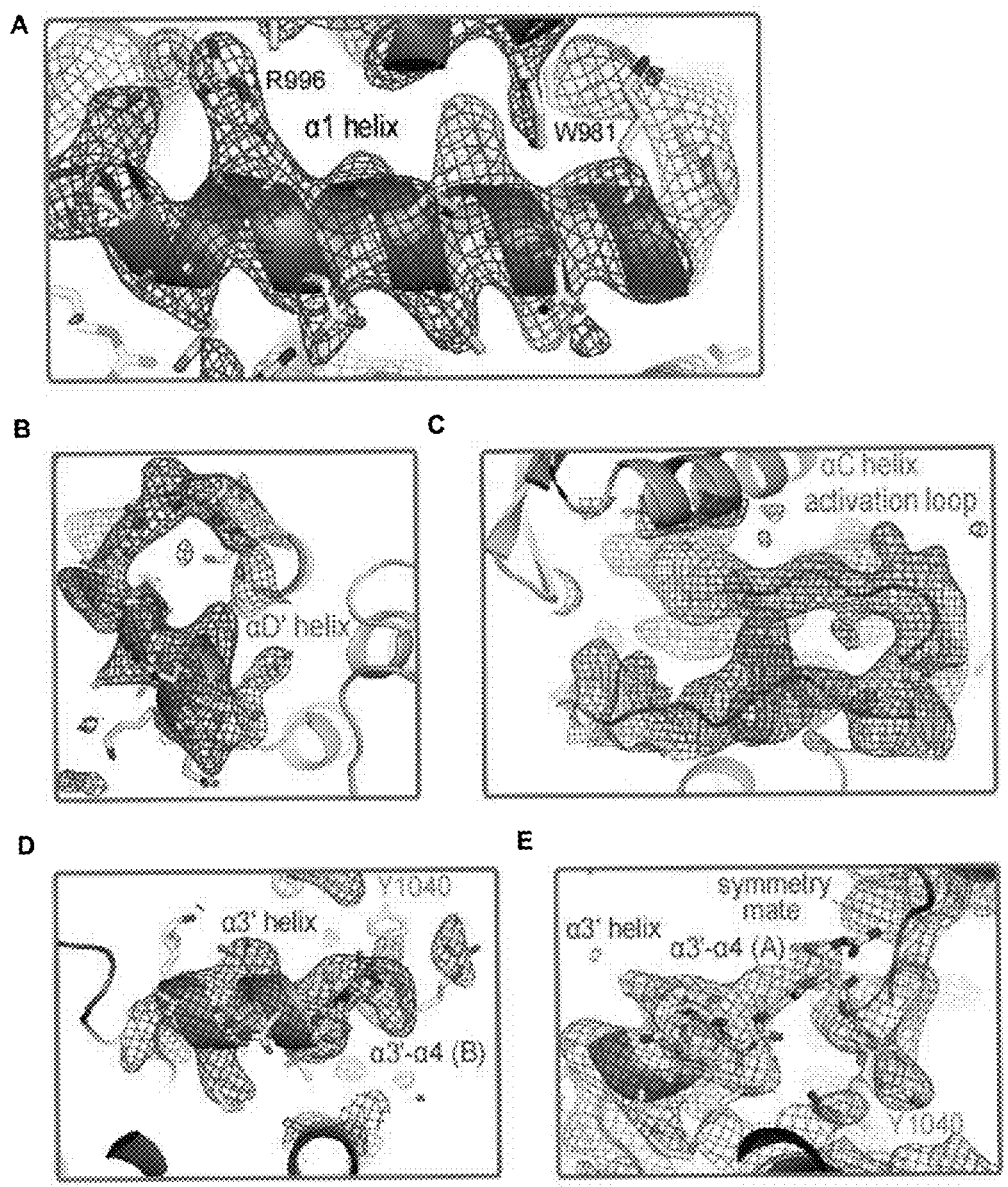
FIG. 9. Examples of electron density of Ire1KR32. A. Side chains of Ire1KR32 resolved at 3.9 Å resolution due to high non-crystallographic symmetry (NCS). B. Electron density map for the αD-helix showing Chain A. C. Electron density for the activation loop of chain A. D. Electron density for the a3' helix and the a3'-a4 loop in an open conformation (chain B). E. Electron density for the a3' helix and the a3'-a4 loop in a closed conformation (chain A).

Tight packing of Ire1KR32 in the oligomer compared to crystal packing of the Ire1-ADP dimer (FIG. 4A, inset) orders several essential elements of Ire1 that could only be built into the present model. These new structure elements are labeled in FIGS. 4C-E. None of the new elements belong to the interface IF1 formed by a two-fold symmetric back-to-back Ire1 dimer (built from monomers A and B, C and D, etc; FIG. 4B) defined in the previously determined structure (FIG. 4C). Two new interfaces form as these Ire1 dimers stack into the helical rod. Interface IF2 is also two-fold symmetric and forms by contacts between the RNase domains of monomers A and D, C and F, etc. It involves the α3' helix and the α3'-α4 loop connecting the α3' and α4 helices. Interface IF3 is formed by a linear side-to-side arrangement of monomers into filaments ( ... →A→C→E→ ... and, with opposite polarity, ... →F→D→B→ ... ). IF3 is formed by contacts between the kinase domains and involves two new elements, the αD' helix and the activation loop (FIG. 4E). Two regions of Ire1, the N-terminal extension (residues 641-664) and the αEF-αF loop (residues 865-892) were disordered in the oligomer, and their structures are yet to be determined. Architecturally, the oligomer resembles the double helix of DNA (FIG. 4B, FIG. 9), where interface IF1 parallels interaction between nucleobases of opposing strands and interface IF3 parallels phosphodiester linkages between nucleobases of the same strand.

The arrangement of the Ire1 monomers at the interface IF3 (FIG. 4E, FIG. 5A) juxtaposes the phosphorylation loop of one kinase and the active side of a neighboring molecule to carry out in-trans phosphorylation. For conventional kinases, the trans-autophosphorylation complex is a dimer wherein kinases exchange their activation loops with a committed partner. In the Ire1 oligomer, the activation loop exchange arrangement is achieved differently such that each kinase offers its activation loop to a new partner, thereby extending the linear filamentous oligomeric assembly.

Figure 10:
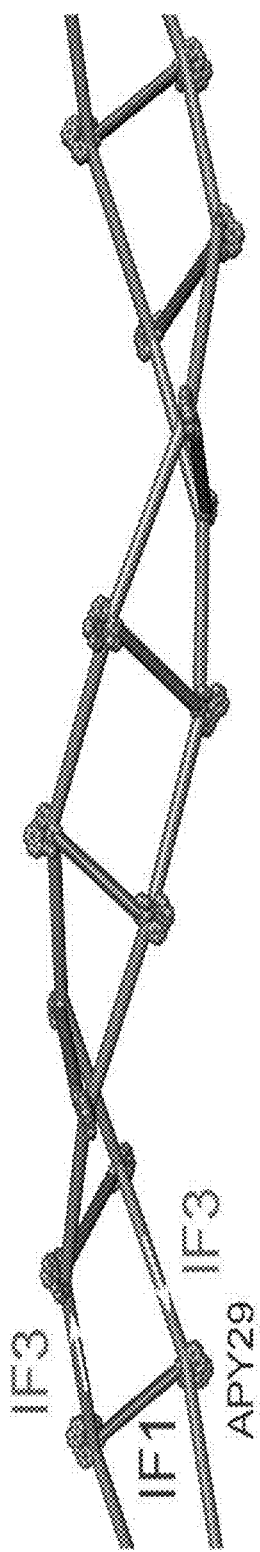
FIG. 10. Double-helical structure of the Ire1 oligomer.
Figure 11:
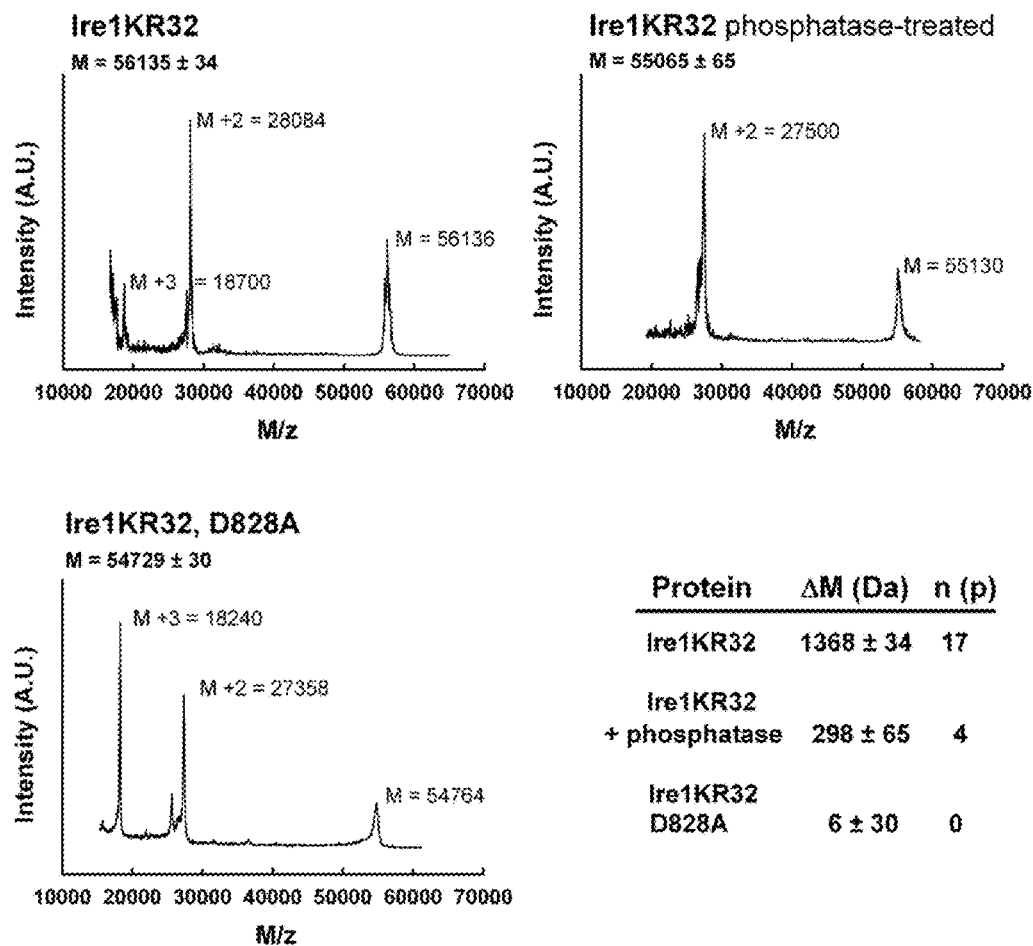
FIG. 11. Mass spectrometry of Ire1KR32 to determine its phosphorylation state.
Figure 12:
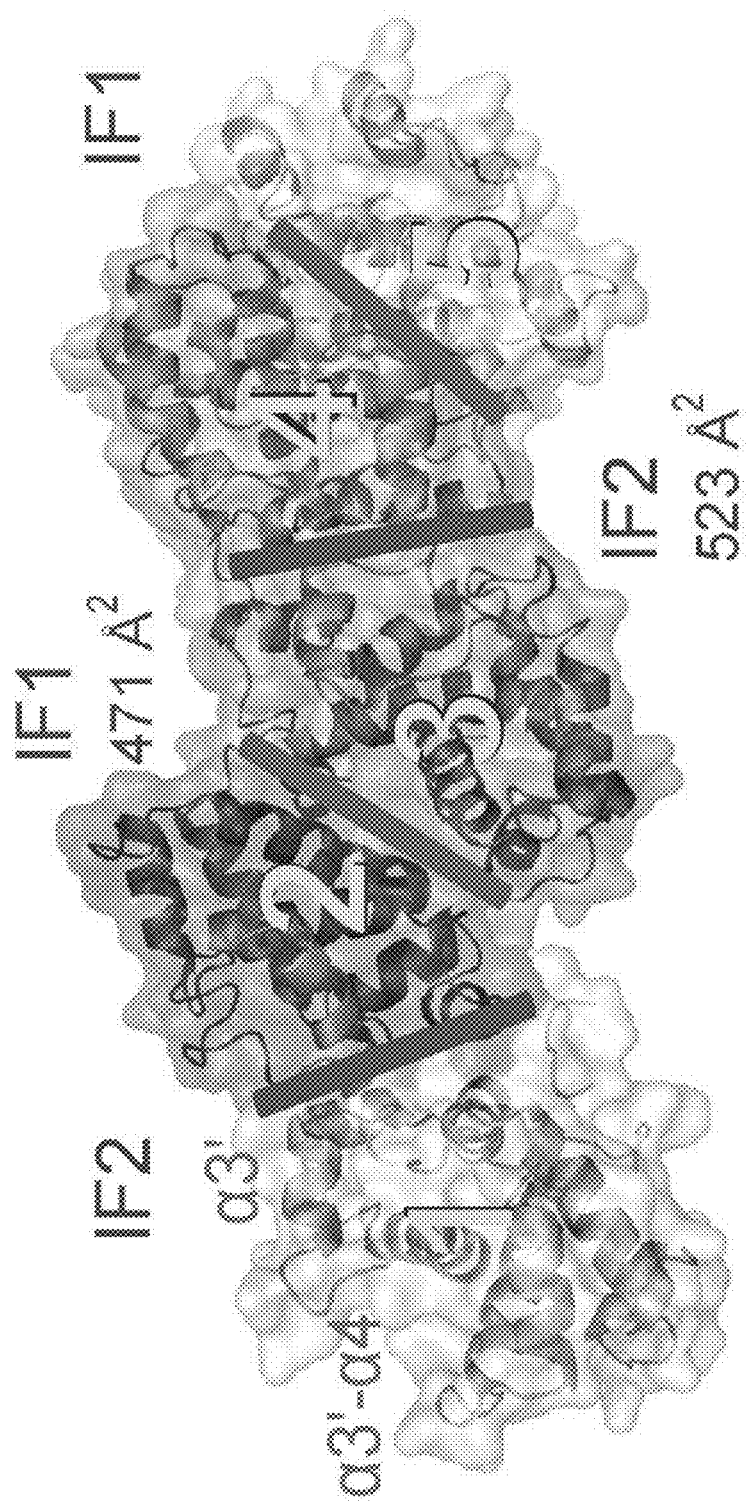
FIG. 12. Oligomeric structure of the RNase domain of Ire1.

Ire1KR32 used in the kinetic analysis and crystallization contained 17 phosphorylated residues (FIG. 10). All but four of the phosphates could be removed by treatment with mixture of phosphatases. Phosphorylation was not observed upon expression of Ire1 with a mutation in the kinase active site (D828A), indicating that all the phosphates of Ire1 derive from its own kinase activity as the protein is expressed in $E.\ coli$. Tryptic digestion followed by mass spectrometric analyses localized the phosphorylation sites to the activation loop and the αEF-αF loop (FIG. 11), both of which face interface IF3. Together, the oligomer structure and MALDI analysis support a model wherein IF3 serves for transfer of the phosphates in-trans. The presence of the interface IF3 resolves the difficulty in explaining trans-autophosphorylation of Ire1 from the sterically unfavorable back-to-back arrangement of the kinases in the IF1-like dimer.

The tightly packed oligomer makes it highly unlikely that kinases other than Ire1 have access to the phospho-acceptor sites, suggesting that the phosphoryl transfer reaction is highly specific. This feature explains both specific phosphorylation of sites in Ire1 that are not part of any recognizable consensus motif and apparent absence of other kinases known to phosphorylate Ire1.

The presence of three distinct interfaces between the molecules of Ire1KR32 in the oligomer structure (FIG. 4, FIG. 5A) raised questions about their relative contribution to activation of the Ire1 RNase. The quantitative cleavage assay with a large dynamic range developed in this work (FIG. 1, FIG. 2) was used to characterize Ire1 variants with each of the interface selectively impaired by mutations. For IF1, Ire1 was prepared with an E988Q mutation that had the strongest deleterious effect among the tested RNase IF1 mutants on the RNase activity. For IF2 and IF3, previously uncharacterized contacts were identified that were mutated such that the respective interfaces should be destabilized (FIG. 5B).

Figure 5:
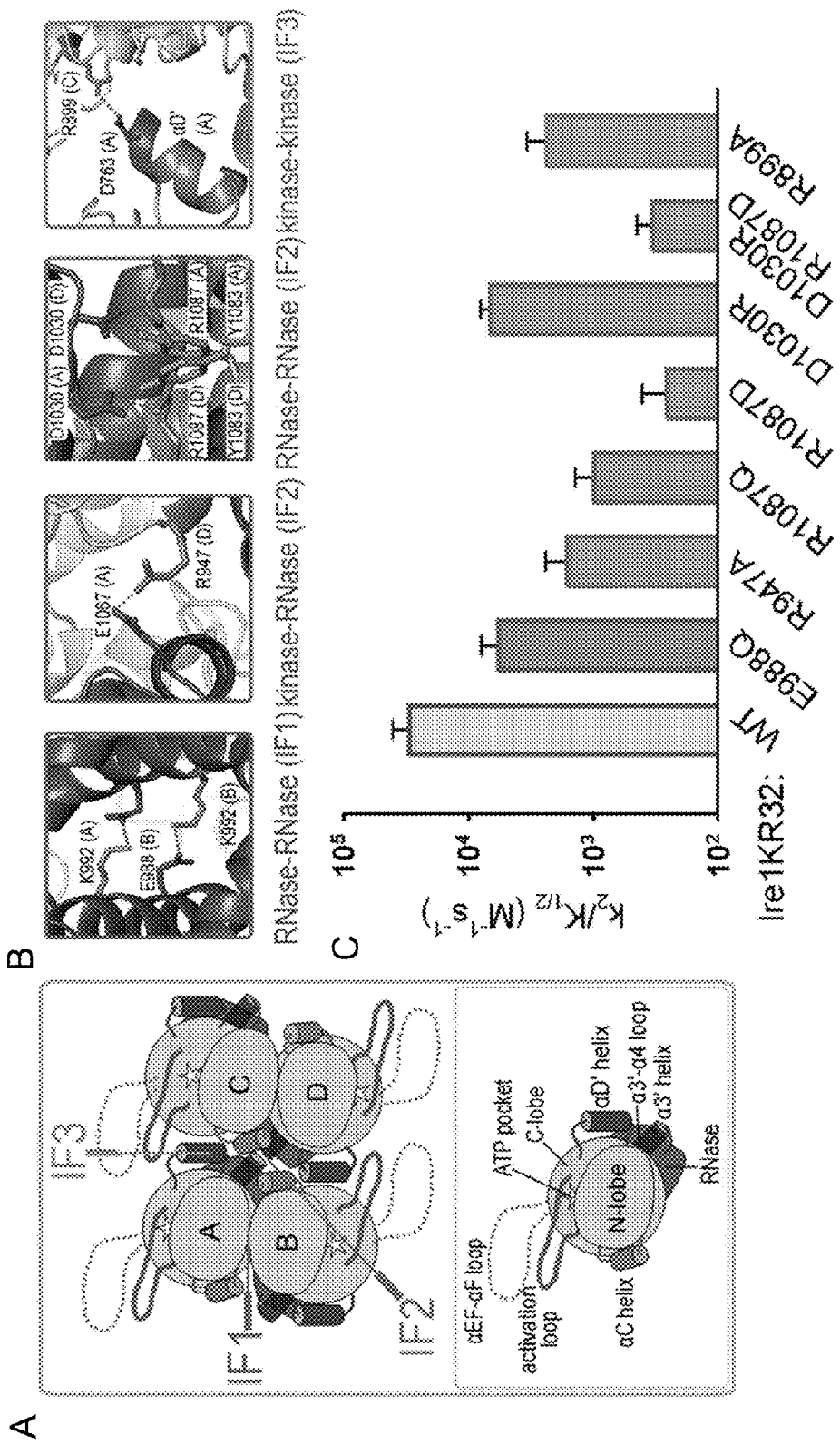
FIG. 5. Three interfaces of Ire1 contribute to the RNase activity. A. Position of the three interfaces and new structural elements of Ire1 within the oligomer. B. Contacts between side chains at each of the three interfaces. C. The RNase activity of Ire1 is significantly reduced upon mutations designed to weaken or disrupt contacts at IF1, IF2 and IF3.

In the standard cleavage assay (3 µM Ire1, HP21 substrate), all mutations tested exhibited significant deleterious effects (FIG. 5C). Mutations mapping to IF2 and IF3 exhibited as strong or stronger effects on the RNase activity as did the E988Q mutation of IF1. A further study was performed of the new interface IF2 formed by the RNase domain of Ire1. Disruption of the salt bridge at the kinase-RNase interface (R947A) resulted in greater than ten-fold reduction of the RNase activity. Mutation of an arginine located at the new RNase-RNase interface (R1087Q) had an even greater effect. As expected for a salt bridge, charge reversal (R1087D) impaired the RNase activity stronger than the charge-neutralizing mutation (R1087Q). The mutation of the partner of R1087 (D1030R) also inhibited the RNase activity, but to a smaller degree. The reason for the smaller impact of the D1030R mutation is unclear. It is possible that D1030R causes re-distribution of local contacts that partially compensates for the disruption of the electrostatic contact. The importance of all three Ire1 interfaces for the RNase activity shows a conjoint effort from IF1, IF2, and IF3 in assembling the activated oligomer of Ire1KR32.

Figure 6:
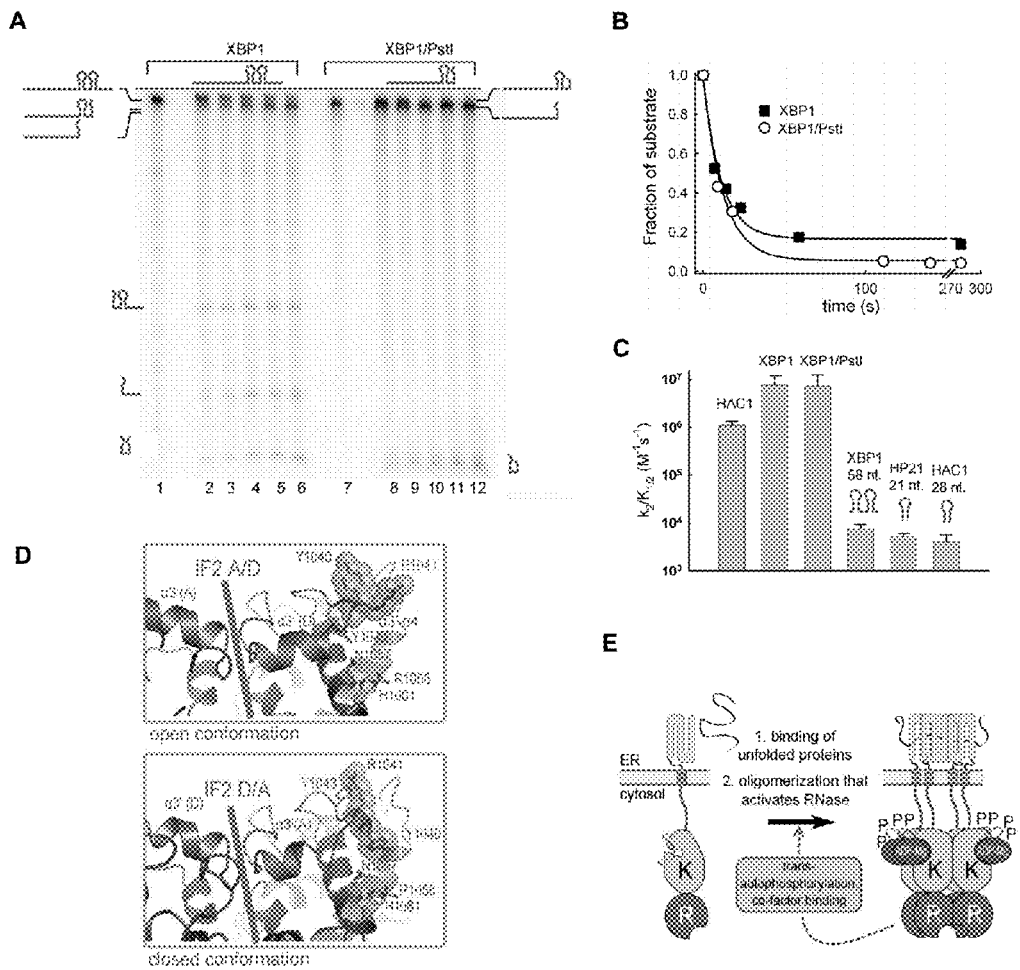
FIG. 6. The model of Ire1 activation. A. Ire1KR32 cleaves truncated XBP1 with a single stem-loop (XBP1/PstI) with the same rate as XBP1 with two stem-loops. B. Quantitation of the gel in (a) and single-exponential least squares fitting of the data. C. Comparison of cleavage rates for substrates with one and two stem-loops. D. Two conformations of the a3'-a4 loop of HLE. E. A general model for activation of Ire1 during the UPR.

It has been suggested that dimerization activates the RNase of Ire1 by providing a tandem arrangement of the active sites that complements the tandem of splice sites in the HAC1/XBP1 mRNA. In principle, this mechanism could explain why stem-loop is cleaved slowly compared to HAC1/XBP1 mRNA (FIG. 2D). However, several pieces of evidence do not support the proposed model further. Although Ire1KR32 exhibits a large advantage for cleavage of HAC1/XBP1 mRNA over stem-loops, Ire1KR and Ire1KR24 show no discrimination (compare HP21 and XBP1 data in FIG. 2D). Therefore, recognition of XBP1 mRNA is linked to the ability of Ire1 to form an oligomer. Furthermore, substrates that contain only a single stem-loop cleavage site can react with Ire1KR32 at a rate of HAC1 and XBP1 mRNA (FIG. 6A, FIG. 6B, compare XBP-1 with XBP1-Pst1), and substrates that contain two stem-loops can react at a rate of HP21 oligonucleotide (FIG. 6C, compare XBP-1, 58 nt. with HP21). These findings suggest that self-association of Ire1 activates the RNase domain by a mechanism different from steric complementation to the dual splice sites in the substrate mRNA.

To better understand the mechanism of Ire1 activation, the arrangement of the RNase domains were examined within the oligomer. In the oligomer structure, the RNase domains are linked into a continuous ribbon by two interfaces, IF1 and IF2. Formation of either interface buries ~500 Å$^2$ of a total surface area (FIG. 14). IF2 involves reciprocal side-to-side contacts between the α3' helices from the adjacent RNase monomers (FIG. 6D). The α3' alpha-helix as well as the α3'-α4 loop connected to the α3' helix (shown in FIG. 6D and FIG. 14) are disordered in the dimer structure suggesting that formation of IF2 stabilizes the α3', α3'-α4 helix-loop element (designated HLE). Point mutation within the HLE strongly inhibit the RNase activity of Ire115. The functional importance of HLE and its location near a dimerization interface may provide a dynamic switch that controls the RNase activity of Ire1. Indeed, the α3' helix forms a part of the proposed active site and creates a cavity characteristic for substrate binding pockets of enzymes. In the absence of HLE, previously proposed active site residues are on a flat solvent-exposed surface (PDB ID 2rio).

While all parts of fourteen Ire1 monomers in the asymmetric unit are related by the non-crystallographic symmetry that defines the Ire1KR32 oligomer, the α3'-α4 loop of HLE is unique in that it adopts two conformations within the oligomer (FIG. 6D). For the majority of Ire1KR32 monomers in the asymmetric unit, an "open" conformation of the loop of HLE is observed (FIG. 6D, top panel). For several monomers, the packing of the helical rods against each other in the crystal lattice cannot accommodate the open conformation. For these monomers, an alternative "closed" conformation has been modeled (FIG. 6D, bottom panel). Only in the open state of the HLE loop would RNA substrate be able to contact the putative active site residues of the Ire1 RNase. In the "closed" conformation, substrate access to the active site, particularly to Y1043 is occluded (FIG. 6D). These observations suggest that the interface IF2 plays an important role in activation of the RNase by positioning the HLE and assembling the active site.

A separate contribution of oligomerization to the RNase activation arises from the large molecular surface created around each RNase active site within the oligomer (FIG. 4A). Such arrangement forms an extensive interaction surface for substrate mRNA not possible with a monomer or a dimer. This explains the finding that only Ire1KR32 that forms oligomers can cleave XBP1 mRNA faster than the stem-loop HP21 (FIG. 2D, FIG. 6C). The dimer-forming constructs, Ire1KR and Ire1KR24, do not discriminate between XBP1 mRNA and HP21 (FIG. 2D). Therefore, oligomerization is linked to the recognition of XBP1/HAC1 mRNA and that extended contacts between Ire1 oligomers and mRNA play out prominently in Ire1 function.

Figure 13:
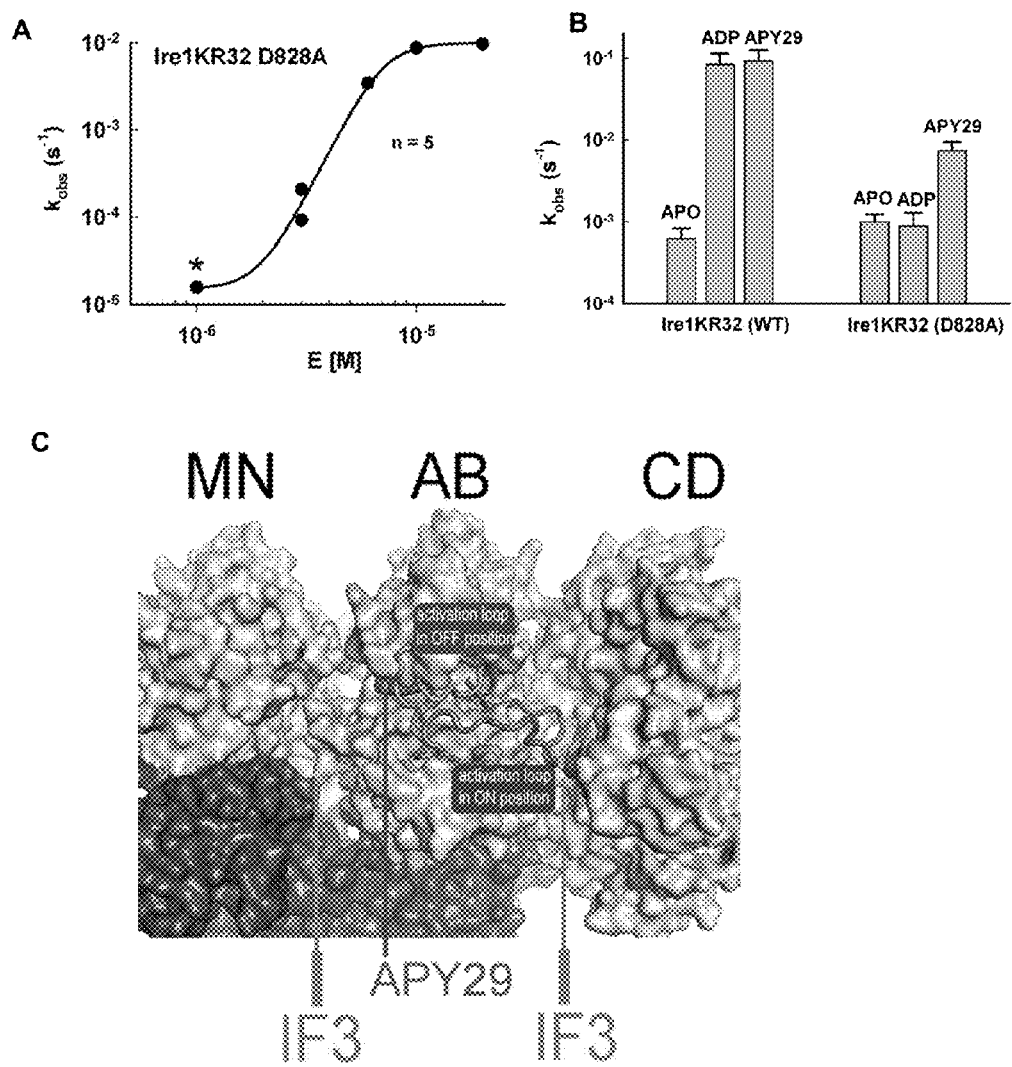
FIG. 13. The role of phosphorylation in activation of Ire1. A. The unphosphorylated variant of Ire1KR32 (D828A) activates by a cooperative oligomerization. B. Unphosphorylated Ire1KR32 has a reduced sensitivity to co-factors. C. Position of the activation loop in the oligomer corresponds to a classic open (phosphorylated) state of CDK2-type kinases.

The key attributes of Ire1 activation have emerged soon after its discovery and include self-association of the receptor, its trans-autophosphorylation, and binding of ADP as a co-factor important for RNase activation (FIG. 1A). The oligomeric structure presented here suggests mechanistic roles for these events. The primary event activating the Ire1 RNase is the self-assembly of the cytosolic domain into a helical nanorod structure induced by binding of misfolded proteins to the LD (FIG. 6E). The isolated cytosolic fragment of Ire1 self-associates independently, indicating that the role of the lumenal domain is to modulate the self-association equilibrium built into the kinase-RNase module. Both trans-autophosphorylation and co-factor binding help Ire1 activation by shifting the equilibrium towards self-assembly, yet neither event is necessary for self-assembly and activation of the RNase. The studies herein show Ire1KR32 can oligomerize and activate without co-factors (FIG. 1D) or phosphorylation (FIG. 10, FIG. 13A, FIG. 13B).

The roles and the temporal separation of the trans-autophosphorylation and ADP binding are now clear. Oligomerization of the unphosphorylated Ire1 positions the kinase for trans-autophosphorylation and stabilizes the activation loop in the open conformation via the interface IF3 (FIG. 9C). ATP binds to the opened kinase, and the activation loop is phosphorylated and stabilized in the open state at the interface IF3. This provides a positive feedback for the oligomer assembly (FIG. 6E). Binding of the co-factor can occur only in the open state of Ire1 kinase, i.e., in an oligomer but not in a monomer. The preferential binding of the co-factor to the open state shifts the equilibrium further toward oligomerization and provides an additional and independent level of positive modulation for the activating transition (FIG. 6E).

An appealing model for the structure of the UPR-induced Ire1 foci11 emerges. Arrangement of the oligomers formed by the LD and the cytoplasmic domains at an angle (FIG. 14A) gives similar periodicity of monomers on both sides of the ER membrane. The resulting cross-linked mesh provides a platform for the formation and unrestrained growth of supramolecular Ire1 foci in two dimensions. The length of the linkers connecting the LD and the kinase-RNase domains to the transmembrane region is sufficient to accommodate such an arrangement. A non-linear response to the input signal and inertia (prolonged time to mount and unmount the UPR) can be expected for such an assembly and may have biological roles that need to be explored.

What is claimed is:

1. A compound having the formula:

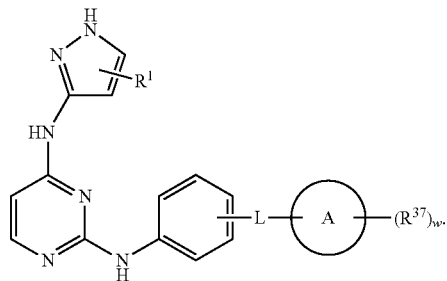

wherein,

R$^1$ is hydrogen, halogen, —CN, —NO, —NO$_2$, —NR$^9$R$^{10}$, —OR$^{11}$, —COOR$^{12}$, —SR$^{13}$, —COR$^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^9$, R$^{10}$, R$^{11}$, R$^{12}$, R$^{13}$, and R$^{14}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L is —NH—C(O)—NH—;

A is aryl or heteroaryl;

R$^{37}$ is halogen, —CN, —CF$_3$, —OH, —NH$_2$, —SO$_2$, —COOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and w is an integer from 0 to 5.

2. The compound of claim 1, wherein R$^1$ is substituted or unsubstituted C$_1$-C$_5$ alkyl, substituted or unsubstituted 2 to 5 membered heteroalkyl, substituted or unsubstituted C$_3$-C$_6$ cycloalkyl, substituted or unsubstituted 5 or 6 membered heterocycloalkyl, substituted or unsubstituted aryl, substituted or unsubstituted heteroaryl.

3. The compound of claim 1, having the formula:

AD75

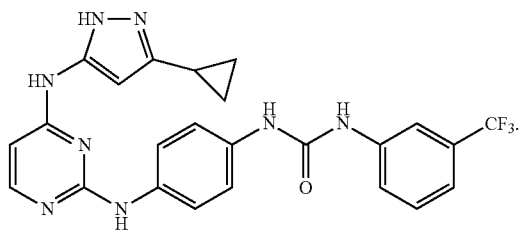

4. The compound of claim 1, having one of the following formulae:

AD75

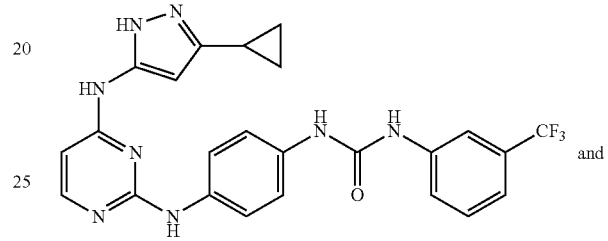

and

AD77

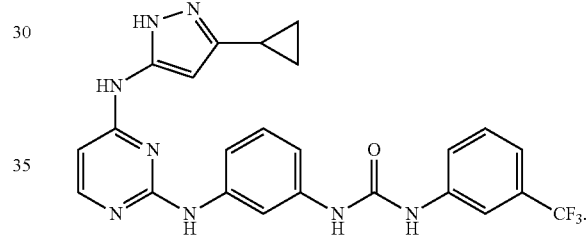

5. The compound of claim 1, wherein R$^1$ is cyclopropyl.

6. The compound of claim 1, wherein A is aryl.

7. The compound of claim 1, wherein A is phenyl.

8. The compound of claim 1, wherein A is a fused ring aryl or fused ring heteroaryl.

9. The compound of claim 1, wherein R$^{37}$ is halogen, —CN, —CF$_3$, —OH, —NH$_2$, —SO$_2$, —COOH, R$^{40}$-substituted or unsubstituted alkyl, R$^{40}$-substituted or unsubstituted heteroalkyl, R$^{40}$-substituted or unsubstituted cycloalkyl, R$^{40}$-substituted or unsubstituted heterocycloalkyl, R$^{40}$-substituted or unsubstituted aryl, or R$^{40}$-substituted or unsubstituted heteroaryl; and R$^{40}$ is halogen, —CN, —CF$_3$, —OH, —NH$_2$, —SO$_2$, —COOH, unsubstituted alkyl, unsubstituted heteroalkyl, unsubstituted cycloalkyl, unsubstituted heterocycloalkyl, unsubstituted aryl, or unsubstituted heteroaryl.

10. The compound of claim 9, wherein R$^{40}$ is halogen, —CN, —CF$_3$, —OH, —NH$_2$, —SO$_2$, —COOH, unsubstituted C$_1$-C$_8$ alkyl, unsubstituted 2 to 8 membered heteroalkyl, C$_3$-C$_7$ unsubstituted cycloalkyl, unsubstituted 3 to 7 membered heterocycloalkyl, unsubstituted aryl, or unsubstituted heteroaryl.

11. The compound of claim 1, wherein R$^{37}$ is substituted or unsubstituted C$_1$-C$_8$ alkyl or substituted or unsubstituted 2 to 8 membered heteroalkyl.

12. The compound of claim 1, wherein R$^{37}$ is unsubstituted C$_1$-C$_8$ alkyl or unsubstituted 2 to 8 membered heteroalkyl.

13. The compound of claim 1, wherein R$^{37}$ is substituted or unsubstituted C$_1$-C$_4$ alkyl.

14. The compound of claim 1, wherein $R^{37}$ is —$CF_3$.

15. The compound of claim 1, wherein w is 0 or 1.

16. The compound of claim 1, wherein w is 1.

17. A pharmaceutical composition comprising the compound of claim 1 and a pharmaceutically acceptable excipient.

* * * * *

SEQUENCE LISTING

```
<160> NUMBER OF SEQ ID NOS: 7

<210> SEQ ID NO 1
<211> LENGTH: 476
<212> TYPE: PRT
<213> ORGANISM: Artificial sequence
<220> FEATURE:
<223> OTHER INFORMATION: Synthetic polypeptide construct including
      Ire1KR32 and N-terminal Pro residue

<400> SEQUENCE: 1

Pro Glu Lys Lys Lys Arg Lys Arg Gly Ser Arg Gly Gly Lys Lys Gly
1               5                   10                  15

Arg Lys Ser Arg Ile Ala Asn Ile Pro Asn Phe Glu Gln Ser Leu Lys
            20                  25                  30

Asn Leu Val Val Ser Glu Lys Ile Leu Gly Tyr Gly Ser Ser Gly Thr
        35                  40                  45

Val Val Phe Gln Gly Ser Phe Gln Gly Arg Pro Val Ala Val Lys Arg
    50                  55                  60

Met Leu Ile Asp Phe Cys Asp Ile Ala Leu Met Glu Ile Lys Leu Leu
65                  70                  75                  80

Thr Glu Ser Asp Asp His Pro Asn Val Ile Arg Tyr Tyr Cys Ser Glu
                85                  90                  95

Thr Thr Asp Arg Phe Leu Tyr Ile Ala Leu Glu Leu Cys Asn Leu Asn
            100                 105                 110

Leu Gln Asp Leu Val Glu Ser Lys Asn Val Ser Asp Glu Asn Leu Lys
        115                 120                 125

Leu Gln Lys Glu Tyr Asn Pro Ile Ser Leu Leu Arg Gln Ile Ala Ser
    130                 135                 140

Gly Val Ala His Leu His Ser Leu Lys Ile Ile His Arg Asp Leu Lys
145                 150                 155                 160

Pro Gln Asn Ile Leu Val Ser Thr Ser Ser Arg Phe Thr Ala Asp Gln
                165                 170                 175
```

```
Gln Thr Gly Ala Glu Asn Leu Arg Ile Leu Ile Ser Asp Phe Gly Leu
                180                 185                 190

Cys Lys Lys Leu Asp Ser Gly Gln Ser Ser Phe Arg Thr Asn Leu Asn
            195                 200                 205

Asn Pro Ser Gly Thr Ser Gly Trp Arg Ala Pro Glu Leu Leu Glu Glu
        210                 215                 220

Ser Asn Asn Leu Gln Cys Gln Val Glu Thr Glu His Ser Ser Ser Arg
225                 230                 235                 240

His Thr Val Val Ser Ser Asp Ser Phe Tyr Asp Pro Phe Thr Lys Arg
                245                 250                 255

Arg Leu Thr Arg Ser Ile Asp Ile Phe Ser Met Gly Cys Val Phe Tyr
            260                 265                 270

Tyr Ile Leu Ser Lys Gly Lys His Pro Phe Gly Asp Lys Tyr Ser Arg
        275                 280                 285

Glu Ser Asn Ile Ile Arg Gly Ile Phe Ser Leu Asp Glu Met Lys Cys
290                 295                 300

Leu His Asp Arg Ser Leu Ile Ala Glu Ala Thr Asp Leu Ile Ser Gln
305                 310                 315                 320

Met Ile Asp His Asp Pro Leu Lys Arg Pro Thr Ala Met Lys Val Leu
                325                 330                 335

Arg His Pro Leu Phe Trp Pro Lys Ser Lys Lys Leu Glu Phe Leu Leu
            340                 345                 350

Lys Val Ser Asp Arg Leu Glu Ile Glu Asn Arg Asp Pro Pro Ser Ala
        355                 360                 365

Leu Leu Met Lys Phe Asp Ala Gly Ser Asp Phe Val Ile Pro Ser Gly
    370                 375                 380

Asp Trp Thr Val Lys Phe Asp Lys Thr Phe Met Asp Asn Leu Glu Arg
385                 390                 395                 400

Tyr Arg Lys Tyr His Ser Ser Lys Leu Met Asp Leu Leu Arg Ala Leu
                405                 410                 415

Arg Asn Lys Tyr His His Phe Met Asp Leu Pro Glu Asp Ile Ala Glu
            420                 425                 430

Leu Met Gly Pro Val Pro Asp Gly Phe Tyr Asp Tyr Phe Thr Lys Arg
        435                 440                 445

Phe Pro Asn Leu Leu Ile Gly Val Tyr Met Ile Val Lys Glu Asn Leu
    450                 455                 460

Ser Asp Asp Gln Ile Leu Arg Glu Phe Leu Tyr Ser
465                 470                 475

<210> SEQ ID NO 2
<211> LENGTH: 443
<212> TYPE: RNA
<213> ORGANISM: Artificial sequence
<220> FEATURE:
<223> OTHER INFORMATION: Synthetic RNA construct

<400> SEQUENCE: 2
gggagaccca agcuggcuag cguuuaaacu uaagcucgcc cuucaccaug acuacaaag      60 acgaugacga caagcuugug guggcagcgg cgccgagcgc ggccacggcg gcccccaaag    120
ugcuacucuu aucuggccag cccgccuccg ucggccgggc gcugccgcuc augauacccg    180
guccgcggga agcagggucg gaggcgagcg ggacaccgca ggcucgcaag cggcagcgcu    240
ugggaaugga cacgcuggau ccugacgagg uuccagaggu ggaggccaag gggaguggag    300
uaaggcuggu ggccgggucu gcugaguccg cagcacucag acuacgugca ccucugcagc    360
```

```
aggugcaggc ccaguuguca ccuccccaga acaucuuccc gugagcaagg gcgaggagcu    420
guucaccggg guggugccca ucc                                           443

<210> SEQ ID NO 3
<211> LENGTH: 354
<212> TYPE: RNA
<213> ORGANISM: Artificial sequence
<220> FEATURE:
<223> OTHER INFORMATION: Synthetic RNA construct

<400> SEQUENCE: 3
gggagaccca agcuggcuag cguuuaaacu uaagcucgcc cuucaccaug gacuacaaag    60
acgaugacga caagcuugug guggcagcgg cgccgagcgc ggccacggcg gcccccaaag   120
ugcuacucuu aucuggccag cccgccuccg ucggccgggc gcugccgcuc augauacccg   180
guccgcggga agcaggguuc gaggcgagcg ggacaccgca ggcucgcaag cggcagcgcu   240
ugggaaugga cacgcuggau ccugacgagg uuccagaggu ggaggccaag gggaguggag   300
uaaggcuggu ggccgggucu gcugagauccg cagcacucag acuacgugca ccuc        354

<210> SEQ ID NO 4
<211> LENGTH: 514
<212> TYPE: RNA
<213> ORGANISM: Artificial sequence
<220> FEATURE:
<223> OTHER INFORMATION: Synthetic RNA construct

<400> SEQUENCE: 4
acuucauggg agcugcagau guuuaagacg gaaaauguac cagagucgac gacgcuaccu    60
gccguagaca acaacaauuu guuugaugcg guggccucgc cguuggcaga cccacucugc   120
gacgauauag cgggaaacag ucuacccuuu gacaauucaa uugaucuuga caauuggcgu   180
aauccagccg ugauuacgau gaccaggaaa cuacagugaa caagaacacu agccccagcu   240
uuugcuuucu gcuuuuuuuc uuuuuuuuuu uuuuagucg ugguucucug augggggagg   300
agccgguuaa aguaccuuca aaagcagaau gcagggguau uggaagcuuu cuuuuuuucu   360
uuuaugcuag uuuuuccuga acaaauagag ccauucuuuu cuuauuacua agaaauggac   420
ggcuugcuug uacuguccga agcgcaguca gguuugaauu cauuugaauu gaaugauuuc   480
uucaucacuu caugaagaca aucgcaagag ggua                               514

<210> SEQ ID NO 5
<211> LENGTH: 21
<212> TYPE: RNA
<213> ORGANISM: Artificial sequence
<220> FEATURE:
<223> OTHER INFORMATION: Synthetic RNA construct for HP21

<400> SEQUENCE: 5
ugcaccucug cagcaggugc a                                              21

<210> SEQ ID NO 6
<211> LENGTH: 28
<212> TYPE: RNA
<213> ORGANISM: Artificial sequence
<220> FEATURE:
<223> OTHER INFORMATION: Synthetic RNA construct for HAC1 28-mer

<400> SEQUENCE: 6
gcuuguacug uccgaagcgc agucaggu                                       28
```

```
<210> SEQ ID NO 7
<211> LENGTH: 58
<212> TYPE: RNA
<213> ORGANISM: Artificial sequence
<220> FEATURE:
<223> OTHER INFORMATION: Synthetic RNA construct for XBP1 58-mer

<400> SEQUENCE: 7
gggucugcug aguccgcagc acucagacua cgugcaccuc ugcagcaggu gcaggccc      58
```